US009603533B2

(12) United States Patent
Lading et al.

(10) Patent No.: US 9,603,533 B2
(45) Date of Patent: Mar. 28, 2017

(54) METHOD OF AND A SYSTEM FOR DETERMINING A CARDIOVASCULAR QUANTITY OF A MAMMAL

(75) Inventors: Lars Lading, Roskilde (DK); David Böttcher Bæk, Søborg (DK)

(73) Assignee: QUALCOMM Incorporated, San Diego, CA (US)

( * ) Notice: Subject to any disclaimer, the term of this patent is extended or adjusted under 35 U.S.C. 154(b) by 820 days.

(21) Appl. No.: 13/985,889

(22) PCT Filed: Feb. 17, 2012

(86) PCT No.: PCT/DK2012/050054
§ 371 (c)(1),
(2), (4) Date: Aug. 16, 2013

(87) PCT Pub. No.: WO2012/110042
PCT Pub. Date: Aug. 23, 2012

(65) Prior Publication Data
US 2013/0331678 A1    Dec. 12, 2013

Related U.S. Application Data

(60) Provisional application No. 61/454,019, filed on Mar. 18, 2011.

(30) Foreign Application Priority Data

Feb. 17, 2011    (DK) .................. 2011 00110

(51) Int. Cl.
*A61B 5/02*    (2006.01)
*A61B 5/021*   (2006.01)
(Continued)

(52) U.S. Cl.
CPC ........ *A61B 5/02007* (2013.01); *A61B 5/0205* (2013.01); *A61B 5/02125* (2013.01);
(Continued)

(58) Field of Classification Search
CPC .................................................. A61B 5/02007
See application file for complete search history.

(56) References Cited

U.S. PATENT DOCUMENTS 4,562,843 A    1/1986    Djordjevich et al.
5,309,916 A    5/1994    Hatschek
(Continued)

FOREIGN PATENT DOCUMENTS

CN    1244779 A       2/2000
CN    101032398 A     9/2007
(Continued)

OTHER PUBLICATIONS

Jan Kips et al., "The use of diameter distension waveforms as an alternative for tonometric pressure to assess carotid blood pressure", Physiological Measurement, IOP Publishing Ltd., vol. 31, No. 4, Apr. 2010, pp. 543-553.
(Continued)

*Primary Examiner* — Christian Jang
(74) *Attorney, Agent, or Firm* — Kilpatrick Townsend & Stockton, LLP

(57)    ABSTRACT

The present invention relates to a method and a system for carrying out the method of determining at least one cardiovascular quantity of a mammal. The method comprises (i) selecting a measuring site of a vessel; (ii) determining or estimating a mean diameter of the vessel at the measuring site; (iii) determining a pulse wave velocity and/or another elasticity related quantity of the vessel at the measuring site; (iv) determining a distension of the vessel at the measuring site; and (v) calculating the at least one cardiovascular quantity from the determined mean diameter, elasticity related quantity and distension of the vessel at the measuring site. The cardiovascular quantity system comprises (i) a plurality of sets of electrodes where each set of electrodes
(Continued)

comprising at least two electrodes can be attached to a skin surface of the mammal such that capacitive coupling through the skin surface and between the electrodes of the set of electrodes is provided when an electrical signal is applied over the electrodes at a measuring site of a vessel; (ii) electrical devices for applying an electric oscillating signal over the respective sets of electrodes; (iii) at least one processor and memory unit arranged to receive signals from the respective sets of electrodes; wherein said at least one processor is designed and programmed to calculate the at least one cardiovascular quantity according to the method using signals from the respective sets of electrodes. By calculating the cardiovascular quantity from such data a more accurate determination can be obtained, which determination further is exempt from the need for any individual calibration or any further type of calibration procedure at all, neither before or after measurements. An accurate determination in this context means a determination with a very low measurement uncertainty, such as in the order of about 10% or less, preferably about 5% or less.

29 Claims, 16 Drawing Sheets

(51) Int. Cl.
*A61B 5/053* (2006.01)
*A61B 5/107* (2006.01)
*A61B 5/0205* (2006.01)
*A61B 5/024* (2006.01)
*A61B 5/0285* (2006.01)
*A61B 5/00* (2006.01)

(52) U.S. Cl.
CPC .......... *A61B 5/0535* (2013.01); *A61B 5/1075* (2013.01); *A61B 5/1076* (2013.01); *A61B 5/7225* (2013.01); *A61B 5/7278* (2013.01); *A61B 5/0022* (2013.01); *A61B 5/024* (2013.01); *A61B 5/0285* (2013.01); *A61B 5/6831* (2013.01); *A61B 5/6833* (2013.01); *A61B 2562/0209* (2013.01)

(56) References Cited

U.S. PATENT DOCUMENTS

| | | | |
|---|---|---|---|
| 6,176,832 B1 | 1/2001 | Habu et al. | |
| 6,443,906 B1 | 9/2002 | Ting et al. | |
| 2002/0019592 A1* | 2/2002 | Mori | A61B 5/0225 600/490 |
| 2005/0283088 A1 | 12/2005 | Bernstein | |
| 2006/0211942 A1 | 9/2006 | Hoctor et al. | |
| 2011/0118564 A1 | 5/2011 | Sankai | |

FOREIGN PATENT DOCUMENTS

| | | |
|---|---|---|
| EP | 0898938 A2 | 3/1999 |
| GB | 2156985 A | 10/1985 |
| WO | 2007000164 A2 | 1/2007 |
| WO | 2010/004940 A1 | 1/2010 |
| WO | 2010004940 A1 | 1/2010 |
| WO | 2010/057495 A2 | 5/2010 |
| WO | 2010057495 A2 | 5/2010 |

OTHER PUBLICATIONS

Peter J. Brands et al., "A Noninvasive Method to Estimate Arterial Impedance by Means of Assessment of Local Diameter Change and the Local Center-Line Blood Flow Velocity Using Ultrasound", Ultrasound in Medicine and Biology, Elsevier USA, vol. 22, No. 7, 1996, pp. 895-905.
Supplementary European Search Report dated Jul. 11, 2014.
International Search Report and Written Opinion—PCT/DK2012/050054—ISA/EPO—May 9, 2012.
Kate Lovibond et al., "Cost-eff ectiveness of options for the diagnosis of high blood pressure in primary care: a modelling study", www.thelancet.com, published Aug. 24, 2011, pp. 1-12.
"Hypertension: Clinical management of primary hypertension in adults", National Institute for Health and Clinical Excellence, NICE clinical guideline 127, Issue date: Aug. 2011, , pp. 1-36.
Gary Drzewiecki et al., "Vessel growth and collapsible pressure-area relationship", Am J Physiol Heart Circ Physiol 273: 1997, pp. H2030-H2043.

\* cited by examiner

METHOD OF AND A SYSTEM FOR DETERMINING A CARDIOVASCULAR QUANTITY OF A MAMMAL

CROSS REFERENCE TO RELATED APPLICATIONS

This application is the national phase under 35 U.S.C. 371 of PCT International Application No. PCT/DK2012/050054 which has an international filing date of Feb. 17, 2012, and also claims priority under 35 U.S.C. 119 to Danish application PA 2011 00110 filed on Feb. 17, 2011, and to U.S. Provisional application 61/454,019 filed on Mar. 18, 2011, which applications are hereby incorporated by reference in their entirety for all purposes as if fully set forth herein.

TECHNICAL FIELD

The invention relates to a method of determining at least one cardiovascular quantity of a mammal, such as blood pressure and/or vascular compliance.

BACKGROUND ART

Most types of prior art methods of measuring cardiovascular properties suffer from the problem that the performance of the measurements and the measurements themselves interfere strongly with the state of the patient, which may lead to erroneous results.

Additionally it is recognized that blood pressure often exhibit considerable variability over time. The newly published guideline by the UK health authorities is in consequence of these facts and the fact that diurnal variations are very important for proper diagnostics of hypertension (NICE clinical guideline 127, August 2011). It has also recently been shown that performing ambulatory blood pressure measurements is overall cost-effective (Lovibond K et al., Cost-effectiveness of options for the diagnosis of high blood pressure in primary care: a modelling study, Lancet. 2011 Oct. 1; 378(9798):1219-30).

Many prior art methods for blood pressure measurements require application of a counter pressure from an external pressure device, e.g. occlusive cuff or other pressure generating devices. These interfering methods generating an external pressure may have a significant impact on the person and the blood pressure. Blood pressure can for example be measured by an invasive pressure sensor, oscillometric or auscultatory tonometric. Blood pressure may also be derived from auxiliary parameters like pulse wave velocity. However, these methods require calibration against a known standard. These methods will inevitably affect the state of the patient, e.g. require surgery or use of an occlusive cuff applying an external pressure to the artery or require that the patient should be in a special position. Furthermore, it is well known that measurements of cardiovascular quantity performed at the office of a medical doctor or at a hospital often are quite erroneous and often consistently higher than when the patient measures it at home. This is normally referred to as the "white-coat syndrome". However, merely the fact that a patient can feel that a measurement is performed will often have a psychological effect which results in a change of state of the patient.

Imaging methods provide information about the structure and dimensions of the limbs measured upon, i.e. the constituting organs and their respective tissues. Methods based on NMR or X-rays will in general have a resolution in space and time that is inadequate for measuring temporal variations on time scales comparable to or smaller than the time of a single pulse and accordingly a reliable determination of arterial distension cannot be based on such methods. Ultrasound may provide for adequate spatial and temporal resolution, but the method will often interfere with the state of the patient and thereby provide unreliable results. Optical coherence tomography can provide for the necessary spatial and temporal resolution, but here the penetration depth is very low. Hence, all the imaging modalities are unsuited for continuous ambulatory measurements and they are also very costly. However, the methods may provide relevant a priori information about the anatomy.

The stiffness (or elasticity) of arteries can be assessed by the pulse wave velocity method where the propagation velocity of pulses along the arteries is evaluated. The basic phenomenon is essentially acoustic. Propagation delays from e.g. the heart to the thighs, the wrist, or the foot are typically measured. However, the propagation length depends on the individual anatomy, which may exhibit considerable variations both in actual length and in vessel diameters. Also the pulse wave propagation velocity depends on the diameter of the artery and on the stiffness of the artery wall. These properties vary along the path from the heart to e.g. the wrist.

U.S. Pat. No. 6,443,906 describes a method and a device for continuously monitoring blood pressure. The method requires that the device is placed close to the wrist and comprises a sensor with a projecting portion—a plunger—which is pressed into the user's body to apply a force to an artery. The counter force on the opposite side of the artery is provided by the radial bone. The device will only function properly with such a positioning and the device exerts a force on the artery and accordingly the method will interfere with the state of the patient.

U.S. Pat. No. 5,309,916 describes a device for measuring blood pressure where the device includes a sensor arrangement which is attached to the exterior of a body and which is electrically conductively connected with an electronic circuit. The sensor arrangement and the circuit are configured to determine, in at least one measuring region of the body, a value which is a measure for a variable that changes periodically over time in the rhythm of the pulse beat, such as the flow velocity, flow quantity, the volume of the arterial blood, a cross-sectional dimension and/or the flow cross section area of an arterial blood vessel. The sensor and circuit further determine a value which is a measure for the pulse wave velocity. By linking the two values together and including at least one calibration value, at least one value that is characteristic for the blood pressure can be determined. A number of different measuring principles are mentioned such as measuring by light or ultrasonic radiation.

As clearly specified in U.S. Pat. No. 5,309,916, the method requires an individual calibration, i.e. the blood pressure of the specific patient should be measured by direct measurement e.g. using an inflatable cuff. Such individual calibration is both cumbersome and may lead to erroneous results. Furthermore it is not described how and which parameters should be related to the calibration measurement. A calibration measurement taking a blood pressure state of the patient, may likely not be reliable for application to correlate determinations of other blood pressure states, which means that a reliable calibration requires calibrating measurements of a large number of different blood pressure states of the same patient.

WO 2007/000164 discloses a method and an apparatus for non-interfering blood pressure measurements. The method and apparatus are based on capacitive sensing where the tissue cross-sections constitute most of the dielectric of the capacitor and where the capacitor forms part of a resonant circuit. However, since the conductivity of blood generally is very high, electrodes that are electrically isolated from the body are needed and calibration is needed. It is noted that the method exploits only the imaginary part of the impedance formed by the electrodes and the material separating the electrodes.

WO 2010/057495 discloses a method for combining distension measurement and pulse wave velocity to obtain a calibrated blood pressure, based on the capacitive sensing method as disclosed in WO 2007/000164. The application does not disclose a direct method for obtaining both the blood pressure variations and the absolute blood pressure.

US 2005/0283088 discloses a method for determining stroke volume from bioimpedance measurements involving the brachial artery but does not involve determining any of the quantities: Blood pressure, vascular stiffness or vascular compliance.

It is an object of the present invention to devise a method that allows for non-invasive determination of one or more cardiovascular quantities, such as blood pressure, wherein the determination does not require individual calibration and which method simultaneously results in highly reliable determinations.

It is a further object of the invention that the method can be performed in a simple manner e.g. by the patient or assistant that does not require special education but merely simple instructions.

These and other objects are obtained by the invention and embodiments thereof as defined in the claims and described herein below.

DISCLOSURE OF INVENTION

The method of the invention is directed towards determining at least one cardiovascular quantity of a mammal, and the method comprises
(i) selecting a measuring site of a vessel;
(ii) determining or estimating a mean diameter of the vessel at the measuring site;
(iii) determining a pulse wave velocity and/or elasticity and/or another elasticity related quantity of the vessel at the measuring site;
(iv) determining a distension of the vessel at the measuring site; and
(v) calculating the at least one cardiovascular quantity from the determined mean diameter, elasticity related quantity and distension of the vessel at the measuring site.

According to the invention it has been found that by calculating the cardiovascular quantity from data comprising the mean diameter of the vessel at the measuring site, the elasticity related quantity of the vessel at the measuring site and the distension of the vessel at the measuring site, a more accurate determination can be obtained, which determination further is exempt from the need for any individual calibration or any further type of calibration procedure at all, neither before or after measurements. An accurate determination in this context means a determination with a very low measurement uncertainty, such as in the order of about 10% or less, preferably about 5% or less.

Accordingly, the method of the invention provides an alternative to the method described in the prior art discussed above, but it also provides a method of determining cardiovascular quantities invasively or non-invasively with a surprisingly high reliability relative to the determination of similar cardiovascular quantities using prior art non-invasive prior art methods.

The term "non-invasive" herein means that the method does not require full penetration of epidermis of the skin of mammals, and "invasive" means that the method does require full penetration of epidermis.

Step (ii) of determining or estimating the mean diameter of the vessel at the measuring site; step (iii) of determining the elasticity related quantity of the vessel at the measuring site; and step (iv) of determining the distension of the vessel at the measuring site may be performed in any order or even—which is preferred—the determinations may be performed simultaneously. One or more of these determinations may be reused for additional determinations. For example in one embodiment the determination or estimation of the mean diameter of the vessel at the measuring site may be reused for additional or consecutive determinations of cardiovascular quantities at this selected measuring site. In one embodiment the determination of the elasticity related quantity of the vessel at the measuring site is reused for additional or consecutive determinations of cardiovascular quantities at this selected measuring site.

In one embodiment the determination or estimation of the mean diameter of the vessel at the measuring site and/or the determination of the elasticity related quantity of the vessel at the measuring site is/are performed less times than the determination of the distension of the vessel at the measuring site, and the determination or estimation of the mean diameter of the vessel at the measuring site and/or the determination of the elasticity related quantity of the vessel at the measuring site is/are reused e.g. in the form of an average of earlier determinations. Thereby the method can provide many consecutive determinations of the desired cardiovascular quantities and in practice the method can deliver continuous or semi continuous determinations of the desired cardiovascular quantities. Due to the simplicity of the method the method in one embodiment delivers continuous or semi continuous determinations of the desired cardiovascular quantities even without the reusing of determinations as described above.

The mammal may be any mammal and in particular a human being. In one embodiment the mammal is a pet, such as a cat, a dog or a horse.

The term "patient" designates the mammal of which the cardiovascular quantity or quantities are determined, whereas the terms "user" or "assistant" designates a person that performs the measurements or helps the patient performing the measurements. Generally the method of the invention is simple to perform and may preferably comprise using a cardiovascular system of the invention programmed to perform the necessary calculations, and the patient will in many situations be capable of performing the measurement him/herself.

The vessel may be any vessel, but is preferably one of the main vessels of the body of the mammal. The vessel is preferably an artery such as a Brachial artery, a Radial artery, an Ulnar artery, a Femoral artery, a Digital artery or a Carotid artery.

The measuring site of the vessel also referred to as simply the measuring site means a site comprises a length section of the vessel, which length section is sufficient long to perform the determination and simultaneously not too long such that the mean diameter does not vary substantially, such as about 10% or more within the length of the measuring site. Preferably, the length of the measuring site is selected such that the time averaged mean diameter of the vessel varies about 5% or less, such as about 3% or less within or along the length of the measuring site. The length of the measuring site is selected in dependence on the type and size of the mammal and in dependence on the mean diameter and the position of the vessel to be measured on. Generally, it is desired that the measuring site has a length of about 30 cm or less, such as about 15 cm or less, such as about 5 cm or less. The minimum length of the measuring site depends on the accuracy and quality of the device which is intended or needed for the determination and optionally perturbations unrelated to the object of the measurement. In one embodiment the measuring site has a length of about 5 mm or more, such as about 1 cm or more, such as about 2 cm or more.

The actual length of the measuring site is determined by a combination of electrode size and distribution of tissues, and when using a set or sets of solely exciting electrode sets, also upon the mutual electrode distances. The field lines penetrating subcutaneous fat will have very little spreading, since fat has a much lower conductivity than muscles and blood. In muscles the field lines will spread out roughly by an amount given by the cross-section of the muscle. Field lines will tend to avoid bones because of the low conductivity and the low permittivity of bones, and thus the contribution from the bones can be eliminated. A calculation of the field distribution can be performed with e.g. a finite element program based on Maxwell's equations for quasi stationary conditions. A detailed equivalent circuit diagram can also be devised in such a way that the conductances and permittivities, respectively, of the lumped impedance elements are given by the electrical properties of the tissues and the physical dimension of the limb or tissue section represented by an equivalent impedance circuit, see further below.

In one embodiment, the measuring site of the vessel is selected to be a site of a vessel, in a limb, in an arm, in a leg, in a hand, in a foot, in a finger, in a neck or in a cardiac region, thoracic cavity, abdominal cavity, pelvic cavity of the mammal. Vessels at these positions have shown to be relatively easy to measure on. The selection of the measuring site may naturally also be made in relation to a desired diagnostic application.

The specific equipment used such as the cardiovascular system of the invention will normally be adapted to one or a number of specific measuring sites, such as 2, 3, 4 or 5 different specific measuring sites.

In one embodiment the measuring site is selected such that the measuring site is substantially free of additional vessels, which may interfere with the determinations.

According to the method of the invention at least three determinations, namely determination of mean diameter, elasticity related quantity and distension of the vessel at the measuring site are performed and preferably using all of these three determinations the one or more cardiovascular quantities are calculated.

The individual determination of mean diameter, elasticity related quantity and distension of the vessel at the measuring site may in principle be performed by any non-invasive method, but preferably one or more of the methods as described below are used.

In one embodiment at least one and preferably all of the determinations of respectively mean diameter, elasticity related quantity and distension of the vessel at the measuring site are performed by a method comprising applying at least one set of electrodes within a selected distance to the measuring site, applying an electrical signal to the electrodes, and providing that electric field lines penetrate the vessel at the measuring site. The electric field lines show the direction of the electric field vector and the density of lines indicates the field strength.

A set of electrodes comprises at least two electrodes. In one embodiment the set of electrodes comprises 3, 4 or more electrodes. In the situation where several sets of electrodes are applied an electrode may for example be a part of a first set of electrodes for one determination and a part of a second set of electrodes for a second determination. Similar electrode constructions are well known to a skilled person.

The electrodes used may each have a size adapted according to the site of the measurement. The size of the electrode should preferably be selected to be so small that its dimension has a negligible impact on the measured distension pulse, but also so large that the current density nowhere has any effect on the tissue. By the term "size of the electrode" is meant the contact area of the electrode to the skin. Examples of electrode size are from about 10 mm$^2$ to about 16 cm$^2$, such as about 1 cm$^2$. In case of electrodes with circular contact area, the contact area may for example have a diameter of about 5 mm or more, such as about 1 cm or more, such as about 2 cm or more. Other electrode shapes than rectangular or circular are feasible, such as elliptic, triangular or shaped according to the specific anatomy of the tissue within the field lines. The mutual spacing between electrodes may for example be about 5 mm or larger, such as about 1 cm or larger or even about 10 cm or larger. The relative displacement of the electrodes is preferably perpendicular to the vessel, which constitutes the object of a measurement.

In order to provide a good electrical contact, the electrodes are preferably placed in close contact with the skin, preferably with a suitable adhesive and/or with a gel that reduces the contact resistance.

In one embodiment each of the electrodes of the at least one set of electrodes are attached to a skin surface of the mammal, preferably by adhesive attachment. The electrodes are applied with a selected distance or distances to each other, either individually directly for application on the skin or preferably on or within one or more substrates. The selected mutual electrode distance or distances can vary according to intended spot on the body to be applied to, and is preferably a set parameter as a basis for the determinations and calculations of the cardiovascular quantities.

Preferably an oscillating voltage or an oscillating current is applied to at least one set of electrodes such that at least some electric field lines between the electrodes intersect the vessel, which constitutes the object of a measurement. The oscillating voltage or the oscillating current is also called the excitation signal.

In one embodiment the excitation signal contains a multitude of frequencies in a range from about 100 Hz to about 10 MHz or higher. The frequencies may be applied simultaneously in parallel or they may be applied sequentially. The relation between voltage and current is given by the impedance of the tissue of the limb between the electrodes, which again is given by the anatomy of the tissues of the limb, the specific conductivities and permittivities of the different tissues of the limb as well as the physical dimensions of the tissues. The conductivities and the permittivities of the different types of tissues vary differently with the frequency.

In one embodiment the method comprises applying at least one set of electrodes within a selected distance to the measuring site, applying an electrical oscillating signal to the set of electrodes and determining at least one impedance parameter over the set of electrodes.

By the invention it has been found that by basing at least one and preferably all of the determinations of mean diameter, elasticity related quantity or/and distension of the vessel at the measuring site on determinations of one or more impedance parameters, unperturbed determinations of desired cardiovascular quantities can be obtained. By introducing impedance sensing as measurement parameter in order to determine one or more of the physical quantities: Mean diameter, elasticity, or/and distension, this provides for a better prognostics and diagnostics value more representative of the subject blood pressure without affecting the state of the subject, and thus ultimately the result thereof.

By the invention, determinations of cardiovascular quantities can be performed with sensors provided on much smaller body areas than prior art methods could be performed on, in particular e.g. when previously using pressure cuffs. In fact, when using only a single set of electrodes, this body-area-usage can be minimized considerably. Further, the electrode areas and also the measuring site may advantageous be reduced in size considerably by proper selection of patch, and/or electrode and/or wiring and/or processor and transmitter/receiver technology, as is known to the skilled person. This decreases the subject's discomfort by wearing the electrodes, e.g. on a substrate.

The impedance variations may in general be converted to distensions $\Delta A$ (or $\Delta d$) by the equation, which has been derived on the basis of an impedance model of the limb (tissues within)

$$\Delta(1/Z) = \sigma_a \frac{\Delta A_a}{l}, \quad (1)$$

l is the length of the vessel part being subject to the field lines by one set of electrodes, $\sigma$ is the Poisson ratio.

The at least one impedance parameter may be measured using a bridge, such as a Wheatstone bridge or a variation thereof; the method preferably comprises automatic balancing the bridge. Bridges of these types are well known in the art.

In one embodiment both the real and imaginary part of the measured impedance(s) are used in the determination of the one or more cardiovascular quantities.

In one embodiment the mean diameter of the vessel at the measuring site is an estimated mean diameter. The estimated mean diameter may for example be estimated for a specific patient on the basis of the type, size, gender, age and/or condition of the patient and/or on earlier determination of mean diameter at the measuring site or at another site of a vessel of the patient.

Vessel dimensions vary significantly from person to person. Merely estimating the mean diameter for a population may therefore lead to cardiovascular quantity measurements of undesired low accuracy.

In one embodiment the mean diameter of the vessel at the measuring site is a determined mean diameter, e.g. based on the measurements. Thereby a more exact mean diameter can be obtained.

In one embodiment an electrical equivalent circuit consisting of resistors and capacitors is established for the impedance. The resistances of the resistors and the capacities of the capacitors of the equivalent circuit depend on conductivities, permittivities, and geometrical dimensions. Measuring the complex impedance as time averaged values at a multitude of frequencies and applying an a priori knowledge about the electrical properties of tissue makes it possible to establish a set of equations from which the time averaged mean dimensions can be inferred and used as the determined mean diameter.

The electrical properties of different types and combinations of tissues and ex vivo are well tabulated in the open literature. However, the conditions encountered in vivo are not in general described and do not in general allow clear separations into the different tissues of the limbs. This is particularly the case when measuring on skin on subcutaneous fat where vascularization in vivo can alter the electrical properties considerably.

Measurements have been completed by applicant performed on living persons at the inside of their upper arm and having subcutaneous fat thicknesses ranging from below 1 mm to above 3 cm and have established this fact. But it also demonstrated that a very simple model for in vivo conditions can be applied, and thus the cardiovascular quantities can be determined based hereupon.

In the frequency range from 1 kHz to 1 MHz one may apply an equivalent circuit consisting of serial and parallel combinations of resistors and capacitors, where the fat permittivity has a weak exponential dependence on frequency with an exponent in the order of 0.1 and a resistance that is almost constant in the regions, where the impedance is predominantly resistive.

In one embodiment the impedance for at least one electrode set is determined in order to for obtain the mean diameter.

In one embodiment one set of electrodes is applied for excitation and another electrode set for detection. Using a separate set of electrodes for detection, i.e. measurement can reduce the influence from skin impedance, but at the expense of introducing the complexity of a four-pole equivalent circuit.

In one embodiment the determination of the mean diameter of the vessel at the measuring site comprises providing an electrical circuit, comprising a set of electrodes being placed such that electric field lines between the set of electrodes penetrate the vessel at the measuring site, applying a plurality of electrical oscillating signals to the set of electrodes wherein the plurality of electrical oscillating signals comprises at least two different excitation frequencies and determining an impedance between the set of electrodes for each excitation frequency.

The plurality of impedance determinations may be measured at different frequencies in the range from about 1 kHz to about 100 MHz. Frequencies above about 100 MHz may be inadequate due to insufficient penetration into the measuring site. In one embodiment, a first frequency (f1) is selected in the range from about 1 kHz to about 1 MHz, a second frequency (f2) is selected in the range from about 1 kHz to about 100 MHz, such as in the range from about 100 kHz to about 100 MHz, a third frequency is selected in the range from 100 kHz to 1 MHz, and an optional fourth frequency is selected in the range from about 10 kHz to about 10 MHz.

In one embodiment the different excitation frequencies comprise a first frequency selected from about 1 kHz, about 12 kHz and about 400 kHz, a second frequency selected from about 12 kHz, about 400 kHz, about 1.6 MHz and about 10 MHz, a third frequency from about 1 kHz, about 12 kHz, about 400 kHz, about 1.6 MHz, and about 10 MHz, and an optional fourth frequency selected from about 1 kHz, about 12 KHz, about 400 KHz, about 1.6 MHZ, and about 10 MHz. Alternatively, excitation with pulses can be applied. The temporal width of the pulses should be equal to or smaller than the reciprocal value of the spectral range that shall be covered. One or more frequencies may be applied, either simultaneously or sequentially.

In one embodiment the method comprises determining the impedances of sets of electrodes for each excitation frequency.

The method of determination of the mean diameter using different excitation frequencies is based on the fact that the electrical properties of fat, muscles and blood, respectively, are very different. At about 400 kHz the permittivities of blood and muscles are almost identical; at about 1 MHz the electrical properties are again different. Other excitation frequencies can be selected in accordance with the composition of the selected limb.

In one embodiment the method comprises at least one set of electrodes for excitation and at least one set of electrodes for detection. In one embodiment, the excitation electrode set may be provided up- or downstreams of the vessel relative to the detection electrodes.

Alternatively, and preferably, one of the electrodes in the excitation set and one electrode of the detection set is provided up- or downstreams of the vessel in relation to the other electrode in the detection set and the other electrode of the excitation set in a crossing configuration, in which configuration only the overlap between excitation field lines and virtual detection field lines will contribute to the measured signal. The influence from subcutaneous fat can then essentially be eliminated from the signal. The crossing electrode configuration is as follows: For each set of electrodes, the electrodes are displaced both in the direction of the artery and perpendicular to the artery in such a way that the connection lines for excitation electrodes and detection electrodes, respectively, crosses each other. The measured admittance, which is the reciprocal impedance, is in this case given by the sum of the muscle admittance and the vessel admittance in the directions of the field lines. This configuration facilitates a simpler estimation of both static and dynamic vessel properties e.g. relative to a configuration with just two electrodes, because the influences from the subcutaneous fat is removed from the calculations. Assuming that both muscle and blood are incompressible implies that with this configuration the distension can quantitatively be related to variations in impedance.

According to the invention it has been found that using both the real and imaginary part of the impedance a much better determination of the mean vessel diameter can be found than when only using either the real part or the imaginary part for the determination of the vessel mean diameter.

In order to perform inverse calculation yielding estimate of vessel mean diameter at the measuring site, it is preferred to provide an a priory estimation of the anatomy at the measuring site and adjacent area penetrated by field lines or subsets of field lines, setting up a set of mathematical equations based on this pre model for an equivalent lumped parameter equivalent circuit for the impedance between the set of detection electrodes, where the mathematical equations represents the combined effect of the impedances along the electric field lines and where at least one length part of field lines passes through skin, one length part of at least one subset of field lines passes through fat layer, one length part of a subset of field lines passes through muscles and one length part of a subset of field lines passes through the vessel and determining the actual length part of field lines passing through the vessel based on the measured impedance between the set of electrodes at the least two different excitation frequencies and the set of mathematical formulas. With separate electrode sets for excitation and detection, respectively, it is the overlap of field lines for the two sets of electrodes that must be considered.

The set of mathematical formulas may for example comprise an equation for each length part of field lines with the length part of field lines as an unknown parameter.

In practice inverse calculation yielding an estimate of vessel mean diameter at the measuring site may be done by using a structural model for the cross section based on the anatomy and comprising the measuring site and adjacent area penetrated by set of field lines, specified by the types of tissue beneath the measuring device, their effective cross-sectional dimensions, the effective penetration areas of the electric field lines therein, and the values of the permittivities and conductivities versus the excitation frequencies. Such a structural model can be established on the basis of an NMR image, on the basis of an image obtained by ultrasound, or an image obtained with x-rays. Such NMR, ultrasound, or X-ray image is of course not necessary for each individual where impedance measurements are to be taken, because only a general structural model is needed for each measuring site in question.

In one embodiment the expression used for determining the mean diameter from the measured impedances can for example be obtained by applying the "Solve" procedure of the program "Mathematica" of Wolfram Research, but other equation solvers known to a person skilled in the art can be applied. A particularly preferred method of determining the mean diameter from the measured impedances is shown in the examples below.

In still another embodiment the arterial dimensions are estimated on the basis of a priori images of the patients e.g. obtained by NMR image, ultrasound, X-ray, multifrequency excitation or a combination of two or more of the mentioned methods.

The distension (also called vascular distension) $\Delta A$ or $\Delta d$ of a vessel is obtained from the temporal variation of the impedance.

In one embodiment of the invention the distension is obtained using a commercial impedance analyzer, by use of which impedance variations, optionally high-pass filtered from low frequency variations, and mean impedance can be determined. However, such an instrument is often unsuited for ambulatory measurements and often is too bulky to be mounted on the patient. Accordingly these methods are not preferred but could be used in the general concept of the method of the invention.

The method of the determination of the distension of the vessel at the measuring site preferably comprises providing an electrical circuit comprising a set of electrodes such that electric field lines between the set of electrodes penetrate the vessel at the measuring site, and determining a temporal variation of impedance between the set of electrodes.

As for the determination of the mean diameter when determining the distension, it is also here preferred to base the determination on both the real part and the imaginary part of the impedance measurements retrieved from the detection electrode or electrodes.

In one embodiment the determination of the distension of the vessel at the measuring site comprises determining the maximal and the minimal impedance between the set of electrodes, preferably the method comprises determining the impedance as a function of time, determining the temporal variation of impedance, and calculating the distension of the vessel at the measuring site.

In one embodiment the method comprises applying at least one set of electrodes within a selected distance to the measuring site, applying an electrical oscillating signal to the set of electrodes and determining at least one impedance parameter selected from mean impedance, minimum impedance, maximum impedance, temporal variations of impedance, impedance as a function of time or a combination of two or more of the before mentioned over the set of electrodes.

In an embodiment there is provided at least one sensor comprising a set of electrodes electrically connected in electrical circuit(s) such that electric field lines between the electrodes penetrate the vessel at the measuring site, the method comprises applying electrical oscillating signals over the set of electrodes and determining at least one impedance parameter of the set of electrodes as a function of time.

In one embodiment a voltage is applied to a set of electrodes and the associated current is measured, for example using the same set of electrodes.

In one embodiment a current is injected by a set of electrodes and the associated voltage is measured, for example using the same set of electrodes.

In an embodiment the method comprises applying at least one set of electrodes within a selected distance to the measuring site, applying an electrical signal, such as an oscillating current and/or voltage of at least one excitation frequency, to the at least one set of electrodes, i.e. the excitation electrode set, and determining the at least one impedance parameter by measuring over said at least one set of electrodes, i.e. the detection electrode set, where the excitation electrode set and the detection electrode set constitutes the same set.

In one embodiment a current is injected by a set of electrodes and the voltage or voltages are measured with different sets of electrodes.

In order to obtain vascular distension at the measuring site time resolved signal measurements are preferably applied. However, if the time averaged diameter is known, it may be sufficient to measure the temporal impedance variations at one frequency.

One embodiment exploits the impedance of one electrode set and an excitation frequency of about 1 MHz. Other excitation frequencies are possible. However, it is preferable to apply a relatively high frequency such as about 100 kHz or higher in order to minimize the impedance effects of the skin. Because of the very small skin thickness capacitive coupling through the skin can be exploited. The effectiveness of this coupling increases with increasing frequency.

Another embodiment exploits two sets of electrodes, one for excitation and one for detection.

The elasticity related quantity can for example be vessel elasticity, vessel stiffness, pulse wave velocity, or other elasticity related quantities from which the elasticity can be calculated, preferably using the mean diameter and/or optionally using the distension.

The determination of the elasticity related quantity of the vessel at the measuring site preferably comprises determining the velocity of a pulse wave in the vessel at the measuring site. The terms "velocity of a pulse wave" and the "pulse wave velocity" or just "pulse velocity" are used interchangeably and mean the velocity with which the blood pressure pulse travels along the vessel.

The propagation of pulses along vessels is essentially an acoustical phenomenon. The pulse wave velocity is much higher than the flow velocity and is for example in the order of 5-15 m/s for the Brachial artery. The velocity is given by the Moens-Korteweg equation. A modified version of this equation, which takes Poission's ratio into account, is as follows $$v = \sqrt{Eh/2\rho r(1-\sigma^2)} \quad (2)$$

Where E is the elastic modulus of the vessel wall, h is the wall thickness, $\rho$ is the blood density, $\sigma$ is the Poisson ratio, and r is the radius of the vessel. It is often assumed that $\sigma=0.5$ and that the wall thickness is typically less than one tenth of the diameter. The term $E \times h/(1-\sigma^2)$ can be determined if v is measured, and r is obtained by evaluating the impedance at several different frequencies. The conversion from distension to pressure change can be performed if the term $E \times h/(1-\sigma^2)$ is known.

Methods of inferring blood pressure from auxiliary parameters like pulse wave velocity and flow velocity are known in the art e.g. the method described in U.S. Pat. No. 5,309,916, in J. G. Thomas, "Continuous pulse wave velocity recording for indirectly monitoring blood pressure in man", Medical and Biological Engineering and Computing, vol. 3 1964, pp 321-322. Such measurements will in general require calibration against a known standard blood pressure measuring device.

In an embodiment the method comprises applying at least two sets of electrodes, a first and a second electrode set, within a selected distance to the measuring site, applying an electrical signal, such as an oscillating current and/or voltage of at least one excitation frequency, to the first set of electrodes, i.e. the excitation electrode set, and determining the at least one impedance parameter by measuring over said second set of electrodes, i.e. the detection electrode set, whereby the excitation electrode set and the detection electrode set constitutes different sets.

In one embodiment the determination of the velocity of a pulse wave in the vessel at the measuring site comprises placing at least two sensors with a selected spacing between the electrodes of the sensors and separated in the direction of the vessel covering a length section L of the vessel comprising at least a part of the measuring site, and determining the pulse as a function of time by each sensor and thereby the velocity of the pulse wave. The sensor may be any type of sensor capable of detecting a pulse. In order to have a high accuracy, the sensor is preferably selected such that it substantially does not interfere with the detected pulse.

Within this application, a sensor is defined as being a substrate comprising at least one excitation and/or detection element, such as one or more electrodes.

In a preferred embodiment there is provided at least two sensors, where each sensor comprises one set of electrodes. The excitation frequencies of the two sets of electrodes may preferably be slightly different in order to avoid undesirable cross-coupling between the two electrode sets. The first frequency may be about 1 MHz or higher and the second frequency may be about 900 kHz or lower. Providing at least two sets of electrodes, each set over a part of the vessel to be measured, provides for a temporal recording of the pulse propagating along the vessel. The spacing between the electrodes may e.g. be from about 1 cm to about 50 cm, such as about 30 cm, about 10 cm or about 3 cm. A small spacing is preferable in order to comply with the required uniformity of the mean arterial diameter, but the determination of the temporal pulse separation becomes more affected by noise, undesirable cross-couplings, and inaccuracies when approaching smaller spacings.

The mean blood density has in the literature been estimated to 1060 kg/m³ for human beings. For other mammals similar mean blood densities can be found by the skilled person.

In one embodiment the pulse velocity is determined by applying three sets of electrodes. One set is placed between the two other sets, also above the vessel and used for excitation. The two other sets are used for pulse detection. The separation of the electrode set is along the direction of the vessel. The electrodes of the electrode sets lie one on each side of the vessel, perpendicular to the extension length of the vessel.

In still another embodiment only one set of electrodes is applied. The delay for determining the quantities is obtained by exploiting a reflection from a bifurcation of the vessel. Reflections in the arterial system are well known to persons skilled in medical professions.

As for the determination of the mean diameter and/or distension when determining the elasticity related quantity, it may also here be desired to base the determination on both the real part and the imaginary part of the impedance measurements, however in most situations distension may be based exclusively on the real part or on the absolute value of the impedance.

The determination of the impedances from the electrode signals may often require special signal processing. A key problem is here that the dynamic part of the impedance is very small in relation to the mean impedance. High performance general purpose impedance measuring instruments can be applied and use thereof is within the scope of the invention. However, prior art high performance general purpose impedance measuring instruments are generally bulky, costly, and do often not provide for adequate temporal resolution and other solutions as described below are therefore preferred.

In one preferred embodiment a Wheatstone bridge adapted to measuring complex impedances is applied. Such bridges have in general shown to be beneficial to apply both when determining mean impedance e.g. for the determination of mean diameter of the vessel and when determining the temporal variation of the impedance, e.g. in order to determine distension.

The bridge is preferably balanced with a feed-back circuitry and is designed as known to a person skilled in the art of servo control as a PID loop. The loop response time is set to be larger than the expected time—also called temporal spacing—between consecutive pulses. A simple adaptive algorithm that adjusts to the minimum rms signal of the bridge may also be applied.

In a preferred embodiment the signal from the electrodes is applied to a quadrature detector as it is known to the skilled person.

In one embodiment there is provided a first set of detection electrodes, a second set of detection electrodes, and a third set of excitation electrodes positioned between said first and second sets of electrodes, the latter being placed such that at least the electrical field lines excited from the third set of electrodes penetrate the vessel at the measuring site, where preferably the third set of electrodes is placed in between the first and second electrode sets.

In an embodiment of the method the determination of the at least one impedance parameter is performed using signal processing by at least one voltage follower and/or instrumentation amplifier for sensing and amplifying the input signal, and at least one mixer in order to demodulate the impedance parameter for quadrature detection of the impedance value of the amplified signals and an analog-to-digital converter to quantizising the analog signal into a digital value.

1. An oscillating current is applied to two electrodes. The electrodes may be the middle set of electrodes in a six electrode configuration. The frequency lies in the 10 kHz to 10 MHz range, preferably in the 100 kHz to 1 MHz range.
2. The voltage of a set of electrodes is evaluated by
   a. Bandpass filtering centered at the excitation frequency.
   b. Mixing (multiplying) the measured signal with an in-phase signal and a quadrature signal both derived from the oscillator. This provides for both the real and the imaginary impedance parts of the signal.
   c. The mixer outputs are lowpass filtered. Mixing and lowpass filtering essentially provides for an additional and very effective bandpass filtering that automatically will be centered at the excitation frequency (ensured by the reference signal from the oscillator). The lowpass filter has a corner frequency much higher than the pulse frequency (e.g. 100 Hz). Transversal filters (finite impulse response filters) are preferably used in order to ensure a constant delay over the frequency range.
3. Normalized correlation functions are calculated for record lengths of e.g. from 2 to 20 sec.
4. A reference correlation function is defined, which may be the correlation function of a skewed saw tooth signal truncated by a Gaussian function.
5. The reference function is fitted to the correlation functions of the signal. The temporal scale is obtained. (Note that both the reference and the correlation functions are normalized, thus the axial scaling is the only fitting parameter.)
6. The reference function is evaluated for each of the fits. The covariance of the correlation function and the reference function is calculated for each of the fits and with the correlation function corresponding to a given fit. A threshold of acceptance is set. A typical value is at 0.7 times the maximum covariance. This initial covariance is obtained while the person is at rest.
7. The temporal locations of the accepted correlation functions are identified and the mean of the maxima and minima, respectively, for the signal and over a time interval corresponding to the interval over which each of the correlation functions are evaluated. The difference yields the impedance variations.

The impedance variations may in general be converted to distensions $\Delta A$ (or $\Delta d$) by the equation, which has been derived on the basis of an impedance model of the limb (tissues within)

$$\Delta(1/Z) = \sigma_a \frac{\Delta A_a}{l}, \qquad (1)$$

$l$ is the length of the vessel part being subject to the field lines by one set of electrodes, $\sigma$ is the Poisson ratio.

In another embodiment the signal processing is performed by a combination of thresholds and zero-crossings. It may be performed as follows:

1. A steady state situation is obtained by letting the subject sit at rest for about one minute.
2. The signal is bandpass filtered (as previously described). The response time of the filter is about ⅓ of the anticipated pulse spacing.
3. The average of the maxima—each recorded on a time-length given by the reciprocal filter bandwidth—is evaluated.

4. The zero-crossings are detected and the occurrence times of the crossings are recorded if the signal within a time of ⅓ of the filter response time (reciprocal bandwidth) exceeds 50% of the peak averaged.
5. A subsequent zero-crossing must not occur before ⅔ times the filter response time for acceptance of the times recorded in 4.
6. The maximum and minimum of signals fulfilling the previous requirements are recorded for the differential impedance and thus pulse pressure.
7. The accepted zero-crossings of signals from two channels (pulse velocity) are applied to estimate time-of-flights.

If two sets of electrodes are positioned on the same limb the impedance loads of the two sets of electrodes may interfere with each other. This may for example be circumvented by temporal multiplexing of the excitation signals.

In an embodiment of bridge detection balancing is provided by simultaneous balancing of the electronic bridges and preferably in conjunction with slightly different excitation frequencies. The preferred excitation frequency is a compromise related to sensitivity and cross-coupling: a relatively low conductivity of blood implies less spreading of field lines along the length of the limp on which a measurement is performed, but it also implies a relatively lower contribution to impedance variations caused by variations of vessel diameter. An excitation frequency of about 100 kHz seems to provide a good compromise.

The temporal spacing between pulses associated with the beating of the heart of the patient can be determined or estimated and in practice a rough estimate is sufficient. For humans the temporal spacing may e.g. be estimated to about one second. For other mammals the temporal spacing may e.g. be estimated to from about 0.1 second to about 10 seconds. The feed-back circuitry implies that the bridge will be balanced. In one embodiment only resistive components are adjusted. A simple impedance calculation shows how an arbitrary change of the complex impedance of the test object can be compensated by the purely resistive components. This embodiment facilitates the use of electronically settable resistors. In an alternative embodiment variocaps can be used as variable capacitors. They can for example be based on reverse biased diodes or on MOS devices.

In one embodiment the method comprises determining or estimating temporal spacing between pulses of the mammal preferably at the measuring site, determining the mean impedance using a bridge and automatic balancing the bridge through a feedback loop with a loop response time that is similar to or larger than the temporal spacing between pulses. The method preferably comprises adjusting at least two resistance components of the bridge.

In one embodiment, the method comprises determining or estimating temporal spacing between pulses of the mammal preferably at the measuring site, determining the temporal variation of impedance using a bridge and automatic balancing the bridge through a feedback loop with a loop response time that is similar to or larger than the temporal spacing between pulses, the method comprises determining temporal variations of the imbalance of the bridge.

In an embodiment for delay estimation in a configuration with three sets of electrodes this is performed by processing the signals from each set of detection electrodes as previously described and cross-correlating the two demodulated signals. The normalized cross-correlation function obtained can then be validated with a reference function as described above. The delay is then estimated from the displacement of the first peak of the validated cross-correlation function. The peak may be inferred by fitting a reference function to the measured function. The reference function may be approximated by a parabola. The excitation is applied to the excitation electrode set placed between the detection electrodes.

In an embodiment for delay estimation this is done by zero-crossing detection and validation as previously described. The delay is inferred from the difference of the zero-crossings of the signals from the two detection electrodes.

A single forward propagating pulse at the Radial artery can be modeled by the following expression:

$$d(t)=a[\sin(2\pi t/t_1)\exp(-(t/t_2)^2)+(1-t)(1-\exp(-t/t_3))]\times [\text{unitstep}(t)-\text{unitstep}(t-1)] \quad (2a)$$

In one embodiment a fitting procedure is applied to provide estimates of $t_1$, $t_2$, and $t_3$. Other mathematical expression can be applied and adapted to the particular place on the body where the measurement takes place.

In one embodiment a relatively simple way of estimating the delay is applied. The spacing between sets of electrodes is selected to be so small that the temporal width of the pulses is substantially smaller than the pulse delay from a first set of electrodes to a second set of electrodes. This will normally imply a spacing of about 15 cm or smaller for human beings.

An estimator is defined by the following expression:

$$\hat{\tau}=\int p'(t)p(t-\tau)dt/\int (p'(t))^2 dt \quad (3)$$

In another embodiment with a spacing between sets of electrodes that is larger than about 15 cm the error using the above estimator may become unacceptable. The estimation is modified to incorporate an iterative procedure like in a Delay Locked Loop where the delay of a delay line is continuously updated by a control loop to match the delay of one signal relative to another signal.

It is noted that those parts of a signal with the steepest gradient with respect to time generally provide for the best determination of the temporal location. It is also noted that the first part of a pulse is considered preferable for pulse wave velocity measurements. These facts imply that for pulse velocity measurements high-pass filtered signals should preferably be applied. The extent to which high-pass filtering can be applied is determined by the possible appearance of small feature differences of the signals and by noise. In an embodiment a high-pass filter up to 1 Hz is applied. In another embodiment high-pass filtering is performed up to 100 Hz.

In yet another embodiment a general procedure is applied: a cross-correlation function is calculated on the basis of measured values and a model cross-correlation function is fitted to the calculated cross-correlation function with the delay as a fitting parameter.

Pulses measured on different subjects will typically be of different shapes because of the effects of reflections and changes of the vascular structure and because distances from the heart to the measuring site are different. The reflections are in general undesirable. The effects can be minimized by filtering the observed pulse with a filter matched to the expected forward propagating pulse.

In certain situations some of the fluctuations may be within the same general bandwidth as the desired signal. Thus it may not be possible to remove these undesirable fluctuations by simple filtering. However, the fluctuations are generally not synchronous with the heartbeat which means that they may be removed in other ways.

This fact can be exploited in several ways and in particular by:

Conditional averaging where a large set of measured pulses are displaced by an amount given by the sum of pulses to a given pulse from a defined reference pulse. These pulses are then averaged. Fluctuations that are not synchronous with the heartbeat will tend to vanish in the averaging process. If pulse characteristics violate preset values, which are adapted from an identified quasi-periodic sequence of the first measured sequence, the sequence may be discarded. The reference pulse can be obtained from an ECG signal, which typically is well defined in time, or from a selected pulse of the impedance signal. It is noted that this procedure may work even if the phase of the pulse exhibits small (less than about 10%) variations.

A scheme similar to a Phase Locked Loop. The oscillator of the loop will in general generate quadrature signals. The quadrature signal is by multiplication with the input signal used for generating an error signal, which facilitates the lock of the loop. The in-phase signal multiplied with the input signal is used as a lock indicator. However, in the present case the signal corresponding to the in-phase signal should not be sinusoidal but a quasi-repetitive signal with a signal form given by the expected pulse shape. The signal corresponding to the quadrature signal can be the derivative of the input signal, a phase displaced version of the signal with a mean of zero. Hilbert transform of a signal has also proven to provide for a good error signal in the loop.

In one embodiment of the method of the invention, the calculation of at least one cardiovascular quantity from the determined mean diameter, elasticity related quantity and distension of the vessel at the measuring site, comprises calculating a systolic blood pressure, calculating a diastolic pressure and/or calculating a vascular compliance.

In order to obtain the differential pressure (the difference between the systolic and the diastolic blood pressure) and the absolute pressure (the diastolic pressure) a relation between pressure and vessel radius is to be applied. The vessel exhibits a nonlinear relation between pressure and radius. At low pressures the vessel is very elastically dominated by the elastin fibers. At higher pressures the vessel appears stiffer; the properties are dominated by collagen fibers. It is also noted that a transmural pressure (pressure difference over the wall) of zero does not imply a zero radius. A negative transmural pressure is needed for a complete collapse of the vessel.

In one embodiment of the calculations the wall may be assumed to be incompressible, thus the cross-sectional area and the mean diameter of the wall are constant. For positive transmural pressures the following relation is applied:

$$P_s = P_1 e^{b(A/A_b - 1)} - P_0 \tag{4}$$

The expression is adopted from: Gary Drzewiecki, Shawn Field, Issam Moubarak, and John K.-J. Li. "Vessel growth and collapsible pressure-area relationship", Am J Physiol Heart Circ Physiol 273: H2030-H2043, 1997, Equation (7a); the cross-sectional lumen area A given by $\pi r^2$. The quantities $P_1$, b, $A_b$, and $P_0$ are constants specific to the subject, e.g. the patient, and to the location of the measuring site upon the mammal.

It is noted that estimation of differential and absolute pressure can be based on other assumed functional relationships of pressure to vessel radius as long as the relationship is monotonic and nonlinear, which means that the gradient does not change sign.

The above given relation of pressure to radius is only valid for $rA \geq A_b$; $A_b$ is the value where buckling will emerge if the pressure is lowered further. Extrapolations made on the basis of experimental data actually imply that $P_s$ as given by Eq. (4) would have to be zero at r=0. This fact implies that Eq. (4) can be simplified to the following expression:

$$P_s = P'(e^{(A/A_b')} - 1) \tag{5}$$

It is noted that an exponential relation can generally be assumed for relations of pressure to vessel cross-section. For very large pressures close to the pressure where the vessel may burst, this relation is no longer valid.

The pulse velocity can be expressed in terms of $\partial P / \partial r \approx \Delta P / \Delta r$ by combining Eqs. (1) and (5), which yields $$v = \sqrt{\frac{\partial P}{\partial A} \frac{A}{\rho}} \cong \sqrt{\frac{\Delta P}{\Delta A} \frac{A}{\rho}} \tag{6}$$

Equation (6) is essentially the Bramwell and Hill equation assuming that the longitudinal expansion of the vessel is negligible. The pulse velocity depends on the radius of the vessel as can be seen from Eq. (1). For relative distensions much smaller than unity the actual value of r can be substituted by the mean value of r. The distension variations are typically smaller than about 10%. For larger variations nonlinear effects may be considered. Nonlinear effects imply a pulse broadening because the velocity decreases with increasing radius. This effect is contrary to the fact that the tapering of the arteries implies a pulse sharpening.

Having measured v, A, $\Delta A$, and obtaining the density $\rho$ from tabulated values facilitates the calculation of $\Delta P$ from Eq. (6).

The absolute pressure can in one embodiment be obtained from Eq. (5). In order to do this the two parameters P' and $r_b'$ are evaluated. Two values of r are known from steps ii and iii namely $\{r, r+\Delta r\}$. Actually a whole range of values for the vessel radius between r and $r+\Delta r$ will usually be known from steps ii and iii, but only two values are needed to determine $\{P', r_b'\}$.

Vascular compliance is defined as the change of vascular volume over the pressure change, i.e.

$$VC \equiv \Delta V / \Delta P = \pi l \frac{r_s^2 - r_d^2}{P_s - P_d} \tag{7}$$

where
l is the length of the vessel part being subjected to the measurement by one set of electrodes,
$r_s$ is the radius of the vessel at the systolic pressure $P_s$ and
$r_d$ is the radius of the vessel at the diastolic pressure $P_d$.

The method of the invention may further comprise determination of one or more additional dimension(s) of the vessel at the measuring site, such as the thickness of a vessel wall, a maximum diameter of the vessel, a minimum diameter of the vessel, a temporal variation of the vessel diameter and/or vessel diameter as a function of time. The additional dimension(s) may be determined using a similar method as when determining the mean diameter.

The method may further comprise determination of pulse rate.

It is generally desired that the method is non-invasive. Preferably, the method does not comprise application of pressure to the vessel. More preferably, the method is substantially non-interfering, preferably such that the patient does not feel it when specific determinations are performed. The method may be performed as a continuous, a semi-continuous or a stepwise determination of the selected cardiovascular quantity/quantities.

The invention also relates to a cardiovascular quantity system for determining at least one cardiovascular quantity in a vessel of a mammal. The cardiovascular quantity system comprises

- a plurality of sets of electrodes where each set of electrodes can be attached to a skin surface of the mammal such that capacitive coupling through the skin surface and between the electrodes of the set of electrodes is provided when an electrical signal, such as a current or a voltage is applied over the electrodes at the measuring site;
- electrical elements for applying the electrical signal, e.g. an oscillating signal over the respective sets of electrodes;
- at least one processor and memory unit arranged to receive electrical response signals from the respective sets of electrodes; wherein processors are designed and programmed to calculate the at least one cardiovascular quantity according to the method of the invention as described above based on the electrical response signals from the respective sets of electrodes.

The sets of electrodes may be as described above. In one embodiment the one or more sets of electrodes are applied on a flexible housing e.g. a patch for example as described in WO 2007/000164 and/or in WO 2010/057495.

The housing/patch optionally in combination with the electrodes may be reusable or disposable. The voltage may be applied from any electrical element e.g. a battery. The power source may be releasably connected to the electrodes, which makes it simpler to apply disposable housing/patch for the electrodes. The electrodes may be fixed to the patch at pre-selected positions.

The cardiovascular quantity system may comprise one or more processor and one or more memory units, where a memory unit and a processor or several of these may be combined in one single unit or they may be in the form of several separate units. The processor or the processors together are designed and programmed to calculate at least one cardiovascular quantity based on signals from the respective sets of electrodes.

In one embodiment the processor or the processors together are programmed to calculate a mean diameter, an elasticity related quantity and a distension of a vessel at a measuring site based on signals from the respective sets of electrodes.

In one embodiment the processor or the processors together are programmed to calculate at least one cardiovascular quantity based on determination of mean diameter, elasticity related quantity and distension of the vessel at a measuring site.

In one embodiment the processor or the processors together are programmed to calculate a systolic blood pressure, a diastolic pressure and/or calculating a vascular compliance based on determination of mean diameter, elasticity related quantity and distension of the vessel at a measuring site.

In one embodiment at least one memory unit is directly coupled to the sets of electrodes for storing determined values of impedance.

In one embodiment at least one processor unit is directly or wireless coupled to the sets of electrodes for pre-processing the values of impedance but without performing a final calculation of a systolic blood pressure, a diastolic pressure and/or calculating a vascular compliance.

The pre-processing preferably comprises determination of at least one of at least one impedance parameter selected from mean impedance, minimum impedance, maximum impedance, temporal variations of impedance, impedance as a function of time or a combination of two or more of the before mentioned impedance parameters over a set of electrodes. In one embodiment the pre-processing comprises determination of a mean diameter, an elasticity related quantity and a distension of a vessel at a measuring site based on signals from the respective sets of electrodes.

In one embodiment at least one memory unit and at least one pre processing processor are incorporated in a local patient unit, the local patient unit may be in direct or in wireless data connection with the respective sets of electrodes. The local patient unit may for example be adapted to be carried by the patient or be adapted to be placed in the patient's home or in the environment where the patient is expected to be. In one embodiment the local patient unit is incorporated in a PC or a mobile phone.

In one embodiment at least one processor incorporated in a main processor unit, which processor or processors are programmed to calculate a systolic blood pressure, a diastolic pressure and/or calculating a vascular compliance based on data obtained from the local patient unit. The local patient unit and the main processor unit may be adapted to provide data communication by a direct connection or a wireless connection. In one embodiment the data from the local patient unit can be transmitted to the main processor unit via Internet.

It is to be noted that although one advantage of the inventive method is that it now is possible to provide accurate measurements on vessels without having to apply a counter pressure to the limb comprising the vessels, it has been realized that the inventive method can also be performed while a counter pressure is in fact being applied. A counter pressure of about 40 mmHg will have a negligible effect on the measurements performed upon the arteries, but will essentially squeeze the veins so that no blood is present herein, which simplifies the determination of the artery cross-section. Measuring the distension as a function of the external pressure applied can also have a diagnostic or prognostic value in its own right.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

All features and embodiments of the inventions including ranges and preferred ranges can be combined in various ways within the scope of the invention, unless there are specific reasons not to combine such features.

Further scope of applicability of the present invention will become apparent from the detailed description of examples and embodiments given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF DRAWINGS

The invention will be explained more fully below in connection with a number of examples and with reference to the drawings.

FIG. 1 shows the system lay-out of an embodiment of the system according to the invention where a sensor patch 1 comprising at least one not shown set of electrodes on a substrate is applied to the skin of a patient proximately to the patient's Brachial artery 2. The patch 1 is positioned in a distance from respectively the Radial artery 3, the Ulnar artery 4 and the Carotid artery 5. The system further includes a voltage or current generator (not shown) providing the electrical excitation signal for the electrodes on the sensor patch 1. The system comprises a reading and processing unit 6, optionally comprising a memory unit, for reading, processing, and optionally storing the measured response from said electrodes. The system may also comprise a computer 6a. The reading and processing unit 6 is wirelessly and/or by wire 7, 8 connected to the sensor patch 1 and/or to the computer 6a. The computer 6a is programmed to perform the desired calculations of the method of the invention and may for example calculate key parameters of medical relevance and provide for a graphical interface. In variations of the system, one or more calculations are performed in the reading and processing unit 6, which can be positioned locally on the patch, and/or be positioned on the subject as shown, and/or entirely remotely, and can be provided by one or more processing units herein.

FIG. 2 shows a typical electrode configuration for measuring impedances at two locations. The electrodes 11a, 11b, 11c, 11d are attached to a patch 10 which e.g. can be attached by adhesive to the skin 9 of the patient. The electrodes 11a, 11b, 11c, 11d are grouped into two sets 12, 13 of electrodes. The electrodes 11a, 11b, 11c, 11d are connected by electrically screened conductive elements 15, such as polymer insulated metal wires to an electronic unit 14. Each set of electrodes 12, 13 consist of two electrodes 11a, 11b; and 11c, 11d, respectively. When four electrodes are applied as shown, two electrodes of a first set may be used for excitation and two other electrodes in a second set may be used for measurements.

An oscillating current generator (not shown), such as a Howland generator or other type of steady current generator is used for excitation of the at least two electrodes in the first set. It may be an advantage to use a current generator in order for the generator to exhibit an almost infinite self impedance. However, a voltage generator or other generator may be applied instead, if the self impedance is then afterwards eliminated in the calculations. Preferably, oscillating electrical energy is used for the electrical excitation.

Figure 1:
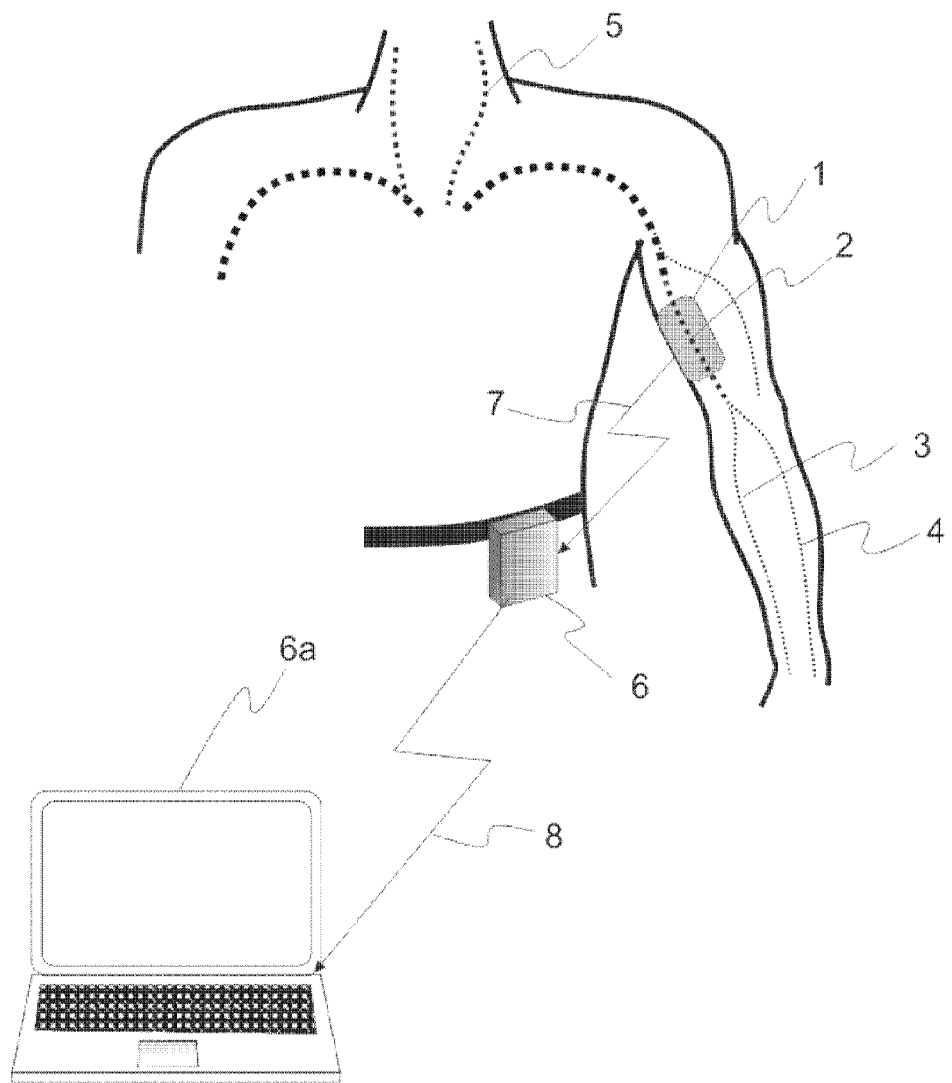
FIG. 1 is a schematic illustration of a cardiovascular quantity system of the invention.
Figure 2:
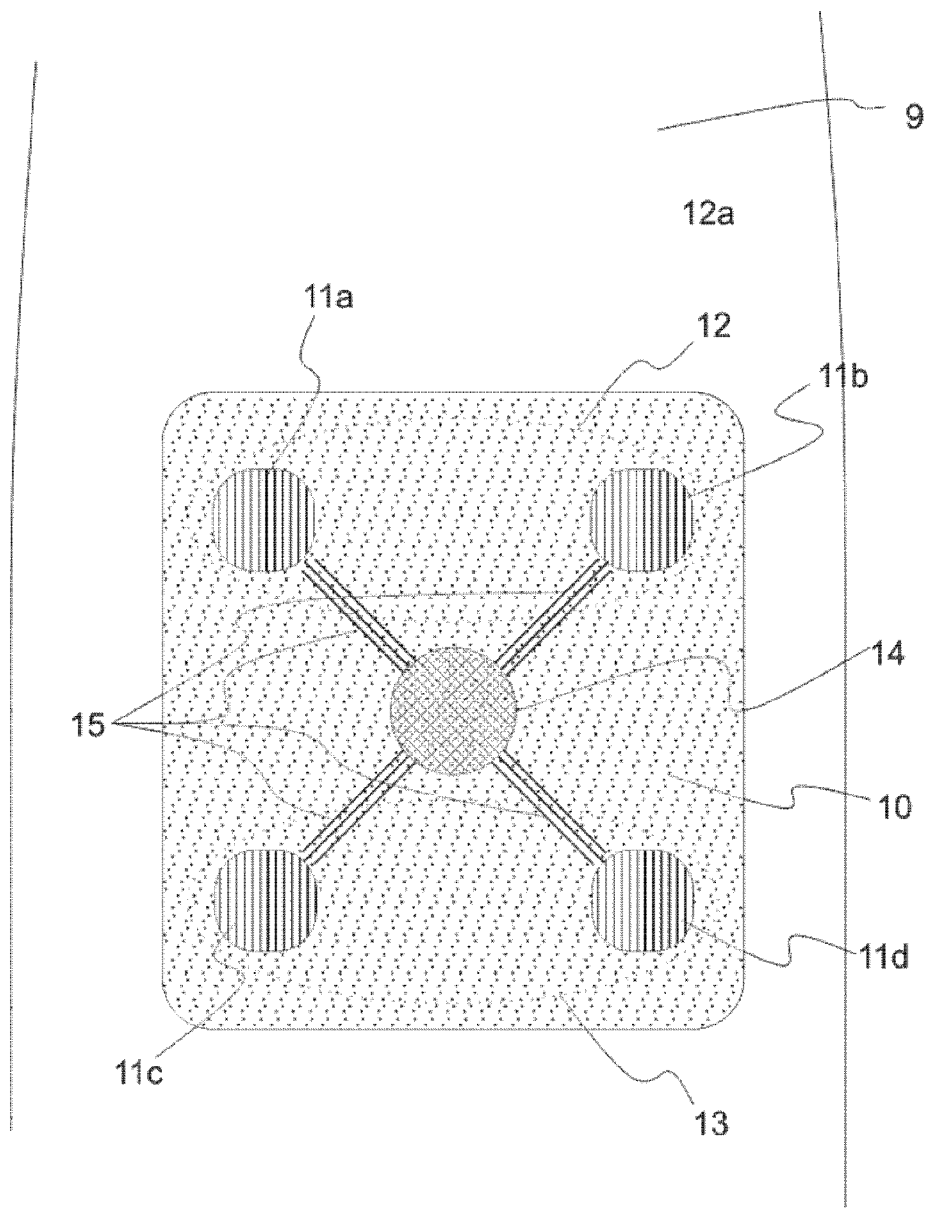
FIG. 2 illustrates an electrode configuration which may be used in the method of the invention.

In FIG. 2, the first electrode set 12 may be used for excitation, and the second electrode set 13 may be used for detection. Alternatively, a cross-link configuration may be used instead, applying excitation current or voltage over electrodes 11a and 11d, and measuring over electrodes 11c and 11b, or vice versa.

Figure 2A:
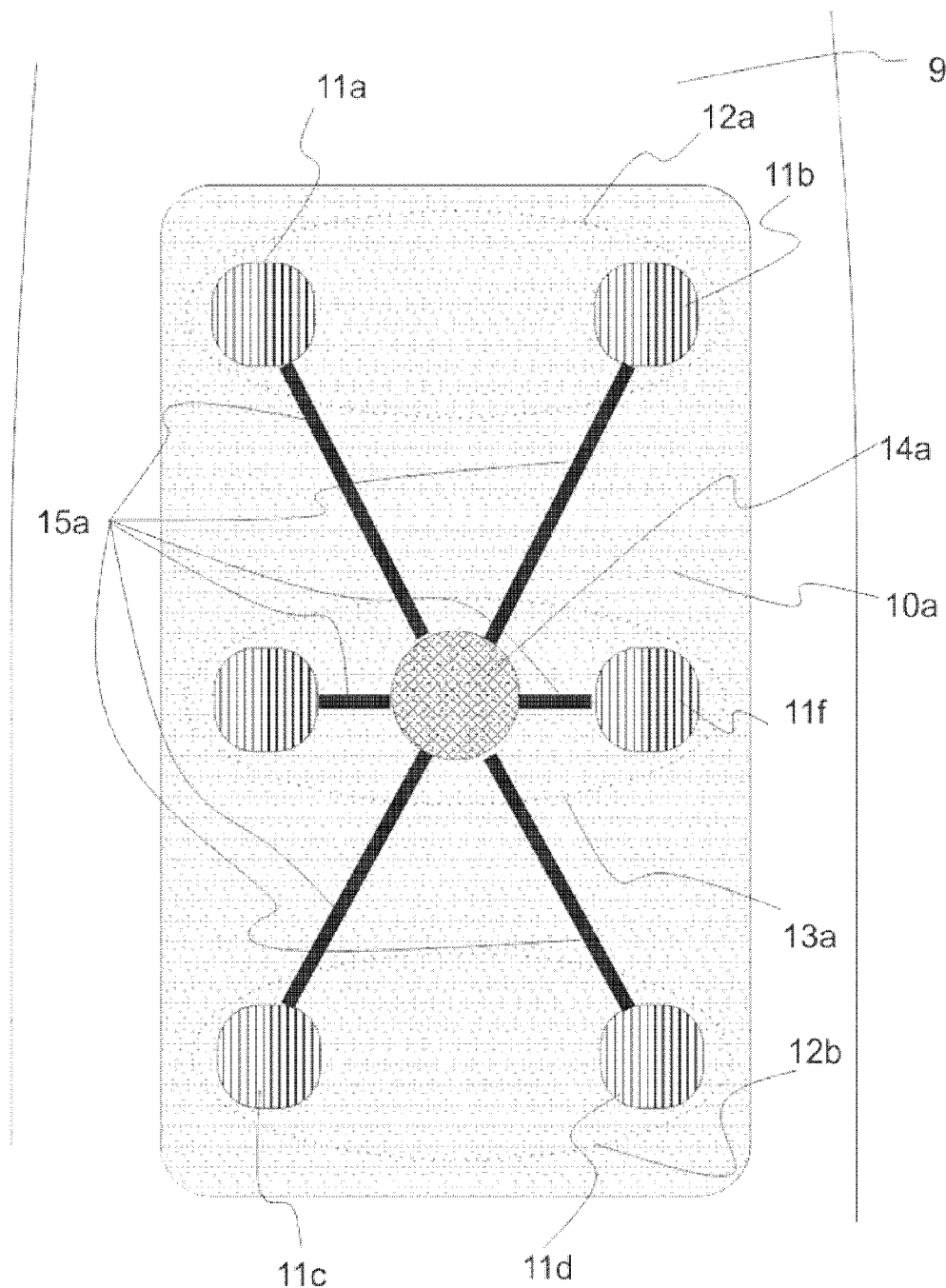
FIG. 2a illustrates another electrode configuration which may be used in the method of the invention.
Figure 3:
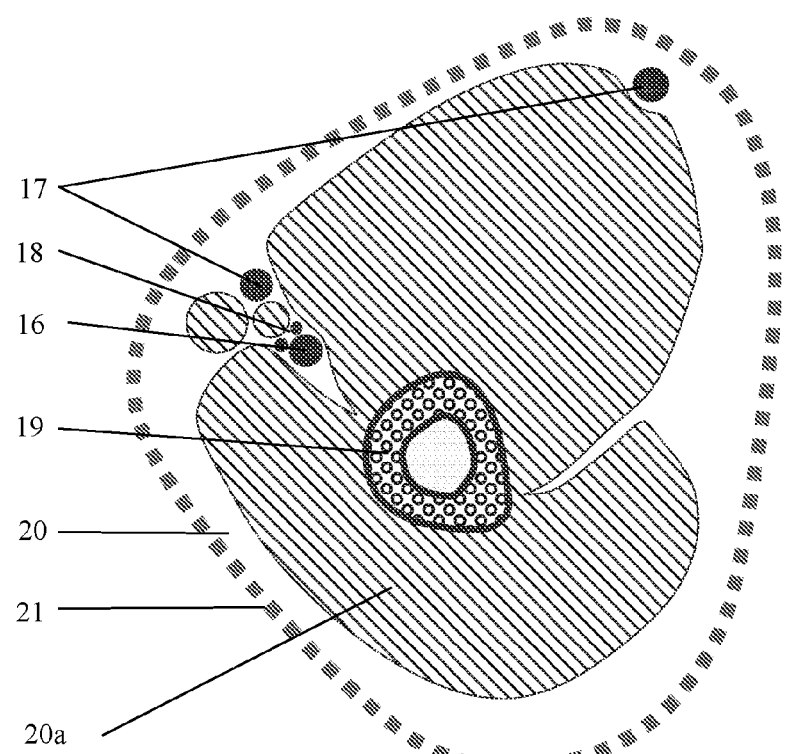
FIG. 3 shows a cross-sectional view of an upper arm in a lateral cut.

FIG. 2a shows an electrode configuration with one electrode set for excitation and two sets for detection, a six electrode configuration. The electrodes 11a, 11b, 11c, 11d, 11e, 11f are attached to or provided in a patch 10a which e.g. can be attached by adhesive to the skin 9 of the patient. The electrodes 11a, 11b, 11c, 11d, 11e, 11f are grouped into three sets 12a, 12b, 13a of electrodes 11a, a first set 12a comprising electrodes 11a, 11b, a second set 12b comprising electrodes 11c, 11d, and a third set comprising electrodes 11e, 11f, respectively. Each of the electrodes 11a, 11b, 11c, 11d, 11e, 11f is connected by electrically screened conductive elements 15a to an electronic unit 14a. FIG. 3 shows a simplified reconstruct of a cross-section in a transversal cut of the upper arm, as may e.g. be obtained with MR imaging, for a healthy young male. It is seen that in the shown cross section the upper arm comprises a Brachial artery 16, veins 17, a nerve 18, a bone 19, a fat layer 20, muscles 20a, and skin 21.

Figure 3A:
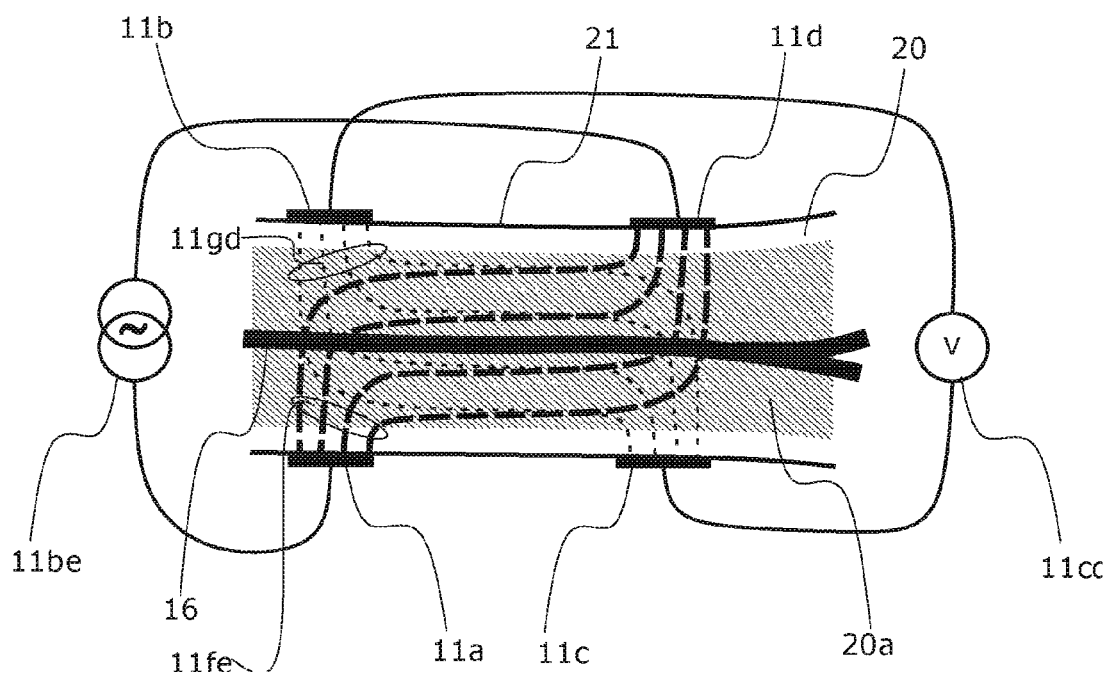
FIG. 3a shows a cross sectional view of an upper arm in a longitudinal cut of an electrode configuration in a method of the invention.

FIG. 3a shows in a longitudinal cut a cross-section of the arm as shown in FIG. 3 being applied two electrode sets, e.g. the two outer electrode sets 12a, 12b of FIG. 2a. Excitation is here illustrated with excitation e.g. from a current or voltage generator positioned on the patch or remotely from the patch, through electrodes 11a and 11d. Thus, an electrode 11a from the first electrode set 12a and an electrode 11d from the second electrode set 12b in a crossing field line configuration is applied here. The current may be applied on electrode 11a and electrode 11d when using oscillating current. The resulting field lines of such type of excitation is indicated with the broken lines life.

Detection is correspondingly performed using electrodes 11b and 11c, e.g. by providing a suitable detection device 11cc over these two electrodes which measures the response to the electrical excitation as given by the properties of the arm. Virtual "field lines" 11gd are indicated on FIG. 3a, which are to be construed as the field lines that would have been associated with electrodes 11b and 11c, if they had been excited.

Such cross configuration of electrodes for excitation/ detection facilitates a determination method wherein the effect of e.g. skin and/or subcutaneous fat is negligible, because it has surprisingly been verified by Applicant by a detailed analysis and verified by a series of measurements that only the region of "overlapping" field lines, i.e. the inner region of the arm, will contribute to the impedance measurement, which effectively "cuts" away the contribution from the exterior subcutaneous fat.

Figure 4A:
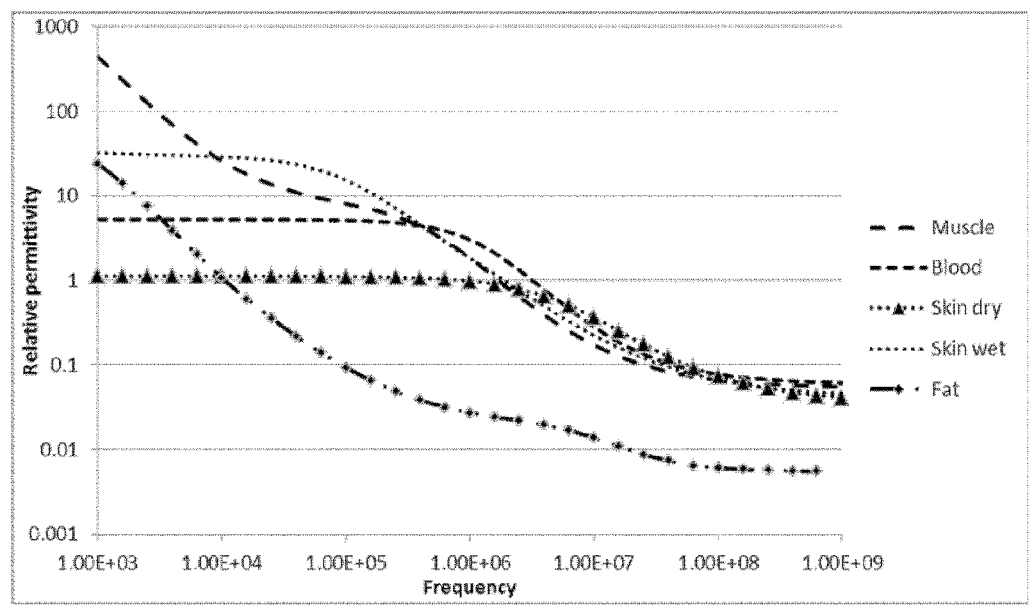
FIGS. 4a and 4b show some values for permittivity (a) and conductivity (b), respectively, as a function of the excitation frequency for different types of tissue.
Figure 4B:
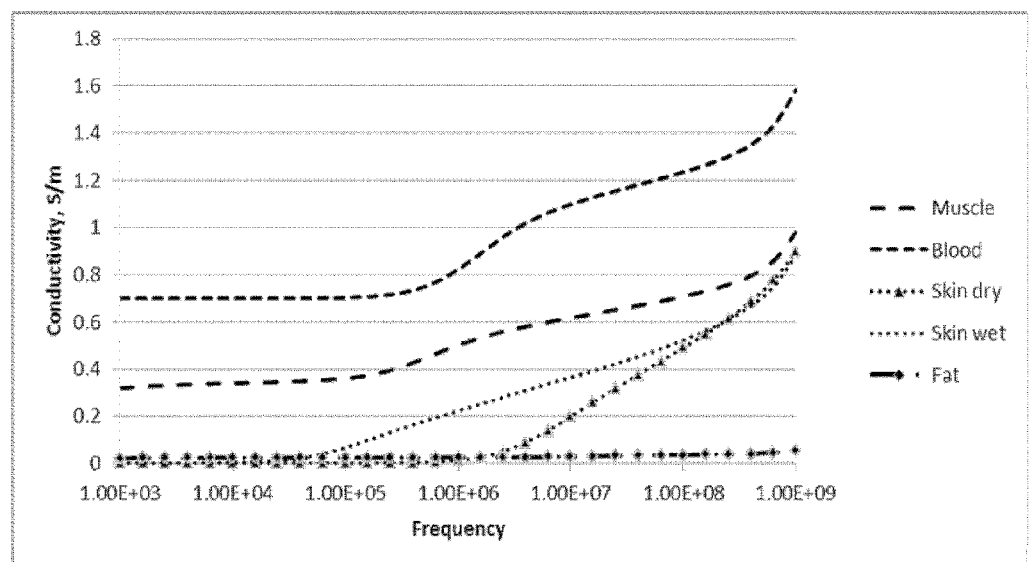

FIGS. 4a and 4b shows typical values for permittivity (a) and conductivity (b), respectively, as a function of the excitation frequency for different types of tissue and for blood as it can be found in the open literature and as provided by models in use today. It has been found during these test measurements that these model values, which have been collected ex vivo, do not apply to vascularised tissues, however correlates well with the model values of blood in vivo.

Figure 5A:
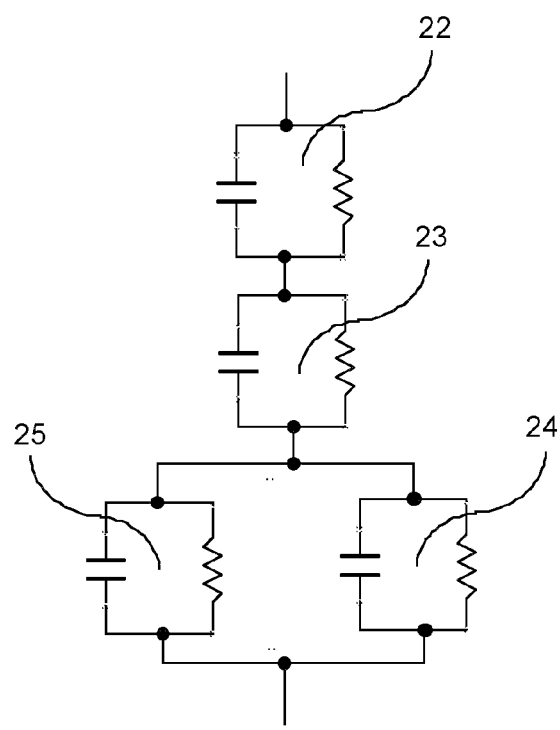
FIG. 5a is a schematic illustration of a first electrical diagram equivalent to the tissue cross-section based on an a priori model for the anatomy.

FIG. 5a shows an electrical equivalent circuit for the impedance between any two electrodes. The electrical equivalent circuit is to be construed as comprising a number of sub circuits 22, 23, 24 and 25 which are set in parallel and/or series in accordance to an a priory estimation of the anatomy at the measuring site and adjacent area penetrated by the field lines of the set of detection electrodes in question. The sub circuits 22, 23, 24 and 25 illustrate a sub circuit 22 equivalent to the skin, a sub circuit 23 equivalent to the outer fat layer, a sub circuit 24 equivalent to the muscles, and a sub circuit 25 equivalent to the blood vessel or vessels. The muscles 24 are in this representation provided in parallel with the vessel or vessels 25. By establishing a set of mathematical formulas for the impedances using such representation the mean diameter of the vessel can be determined based on impedance measurements at a number of different oscillation frequencies.

Figure 5B:
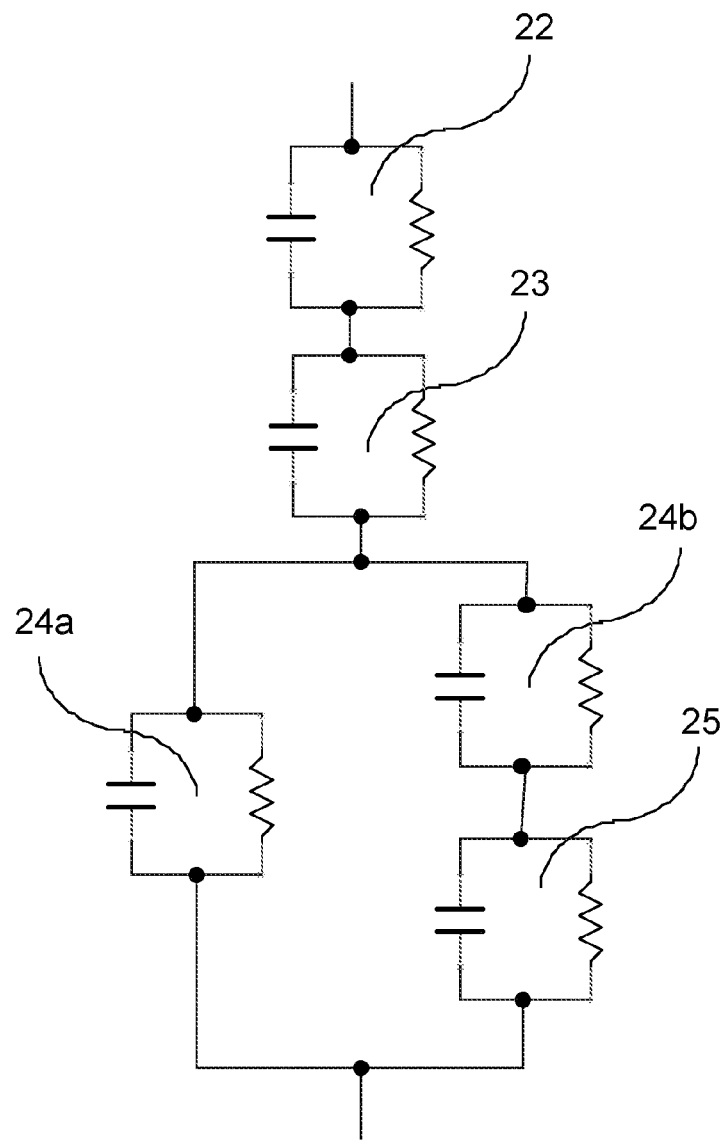
FIG. 5b is a schematic illustration of a second electrical diagram equivalent to a tissue cross-section based on an a priori model for the anatomy.

FIG. 5b shows another electrical equivalence circuit, wherein the representation is further detailed. The sub circuit 24b in series with the vessel or vessels 25 represents the part of the muscles in the arm, which are entered into by the field lines of one set of electrodes at the same line-of-view as the vessel or vessels 25, which are being measured upon, i.e. mainly the Bracial artery 16. The remaining muscle part contribution is provided as a sub circuit 24a in parallel with the "seen" muscle part 24b and the vessel or vessels 25.

Figure 6:
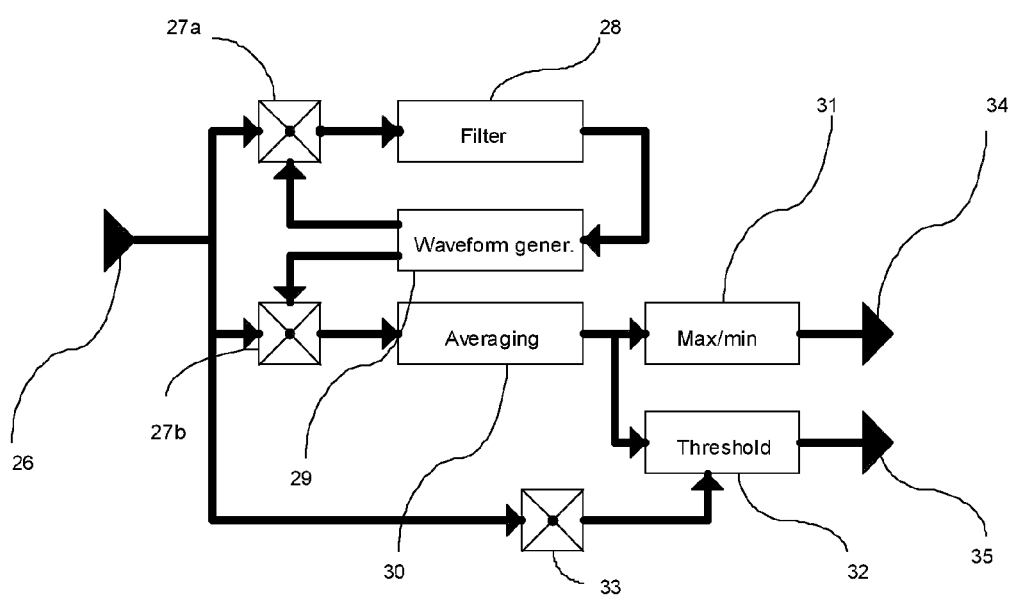
FIG. 6 is a schematic illustration of determining a temporal variation of impedance using a bridge.

FIG. 6 illustrates a concept of a signal processing loop to track the phase of the signal, validate its coherence with the heartbeat and evaluate the impedance variations that are synchronous with the heartbeat. The signal processing loop and related loop comprise a first and a second multiplier 27a, 27b, an integrating and a low-pass filter 28, a waveform generator 29 that provides quadrature outputs, an averaging circuit 30, a maximum and minimum detection circuit 31, a threshold validator 32 and a squaring and averaging unit 33.

The input signal 26 is the detected impedance signal, e.g. over the detection electrode set 11b, 11c, which is fed to the loop system. The waveform generator 29 generates two signals where the repetition frequency is controlled by the output of the integrating and low-pass filter 28. The signal for the second multiplier 27b, which is not a part of the loop, is the expected pulse signal having a fixed amplitude; the signal entering the first multiplier 27a, which is a part of the loop, is orthogonal to the signal 26 in such a way that the averaged multiplier output of the first multiplier 27a provides an error signal: If the repetition frequency is higher than the pulse frequency, the error signal is negative and if the repetition frequency is lower than the pulse frequency, the error signal is positive. If a proper i.e. an accepted input signal exists, the waveform generator 29 will generate a signal of the same repetition frequency. By multiplying the in-phase signal of the waveform generator with the input signal 26 and averaging by the averaging circuit 30 in order to eliminate higher harmonics, a correlation of the input signal 26 and the signal of the waveform generator is obtained as an output signal from the averaging circuit 30. A maximum/minimum detector 31 will then provide outputs 34 representing the maximum and minimum impedances measured, corresponding to the systolic pressure and diastolic pressure, respectively. The output signal from the averaging circuit 30 is also validated in the threshold validator 32 and only accepted if the averaged output of the second multiplier 27b normalized with the input signal power exceeds a pre-set threshold. The input signal power is obtained from the squaring and averaging unit 33, which implies squaring and averaging of the input signal 26.

Figure 7A:
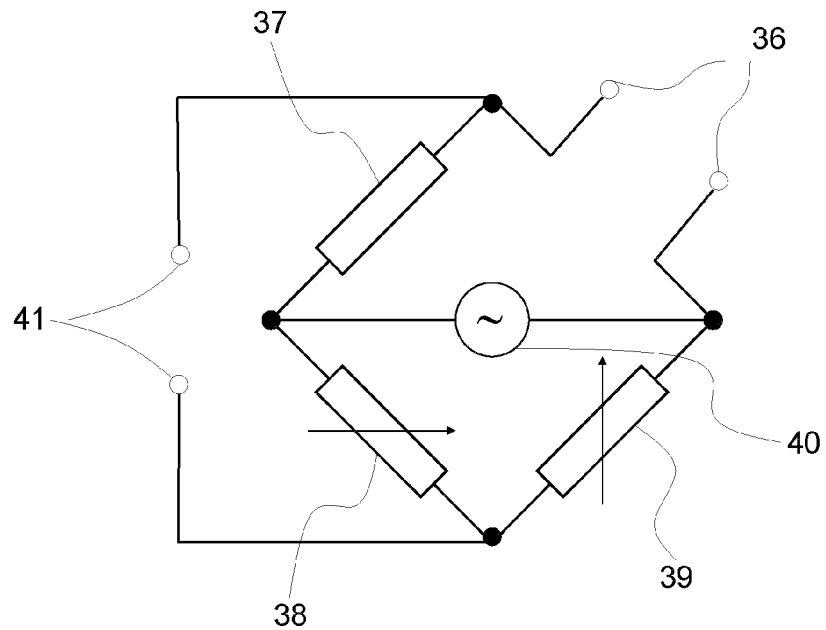
FIGS. 7a and 7b are schematic illustrations of determining mean impedance and impedance fluctuations using a bridge.
Figure 7B:
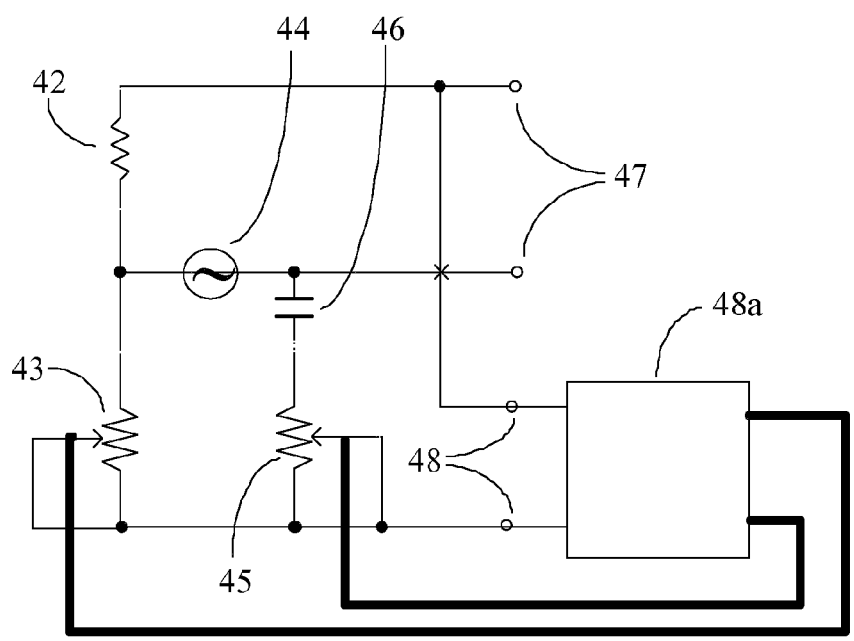

FIGS. 7a and 7b illustrate the use of impedance bridges for extracting both the mean impedance and the impedance fluctuations of the detected values. FIG. 7a shows a bridge with one fixed impedance 37 and two adjustable impedances 38, 39 and an object impedance 36, i.e. the subject impedance. An excitation signal is provided by generator 40. The balance of the bridge is measured at measuring position 41. The adjustments may be performed manually, but are preferably performed automatically over the measurement time period, e.g. by a processing unit.

FIG. 7b shows a alternative type of bridge realisation providing the advantage of regulating the impedances automatically, resulting in a higher resolution of and the removal of disturbances in the output signal. The adjustable impedances 43, 45 are preferably purely resistive. The fixed impedance 42 is also preferably purely resistive. With the capacitor 46 it is possible to compensate for any arbitrary impedance 47. The excitation signal is provided by the current generator 44 and the bridge balance is measured at measuring position 48. A control device or processor 48a provides settings of the adjustable impedances 43, 45 respectively, based on the bridge balance signal measure at the measuring position 48.

The skilled person is also familiar with other types of bridge and non-bridge signal measurement methods known in the art, which may be applied in order to measure or illustrate the impedances over the measurement electrodes. Any suitable of these may be applied or combined with the present invention.

Figure 8A:
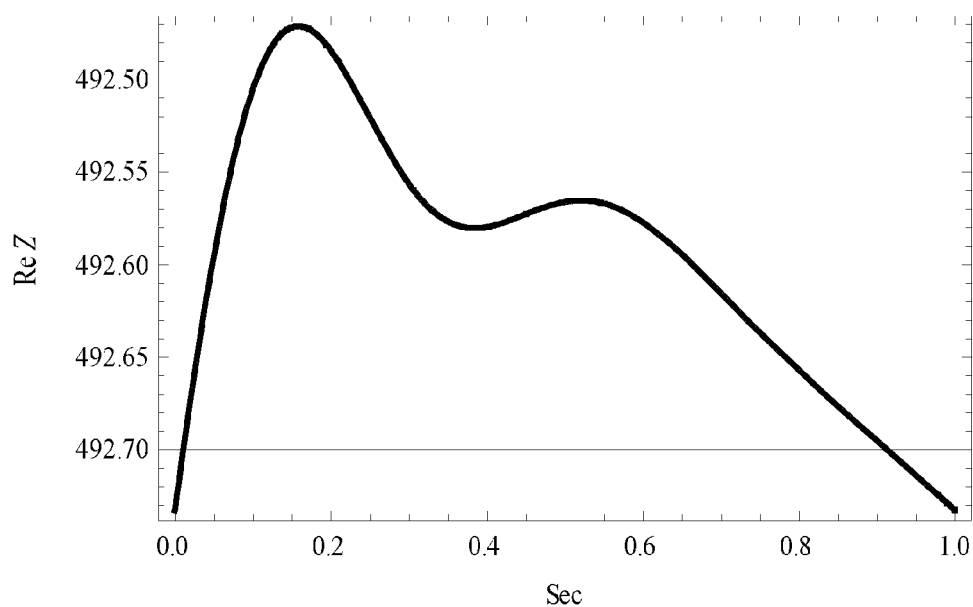
FIGS. 8a and 8b are schematic illustrations of calculated variations of the real (a) and the imaginary (b) parts of the impedance, respectively, associated with a heartbeat.
Figure 8B:
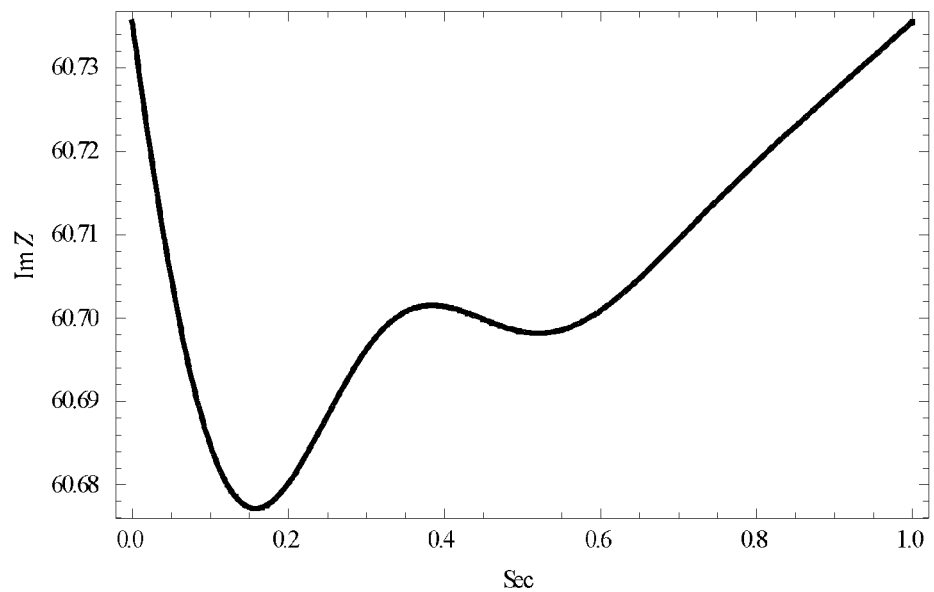

FIGS. 8a and 8b shows the calculated variations of the real (a) and the imaginary (b) parts of the impedance, respectively, associated with a heartbeat.

Figure 9A:
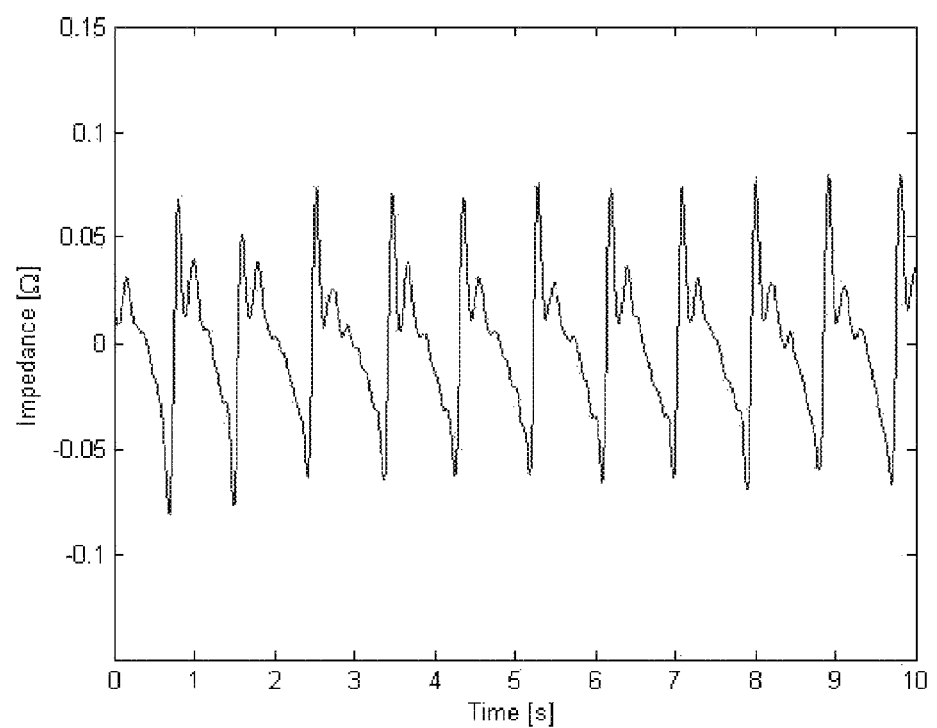
FIG. 9a is an illustration of temporal variations of the absolute value of a measured impedance for one electrode configuration.

FIG. 9a shows a trace of the temporal variations of the absolute value of the impedance measured with electrodes placed between the Biceps and Triceps muscles. Each electrode area is around 100 $mm^2$ and the spacing between the centres of the electrodes is around 30 mm.

Figure 9B:
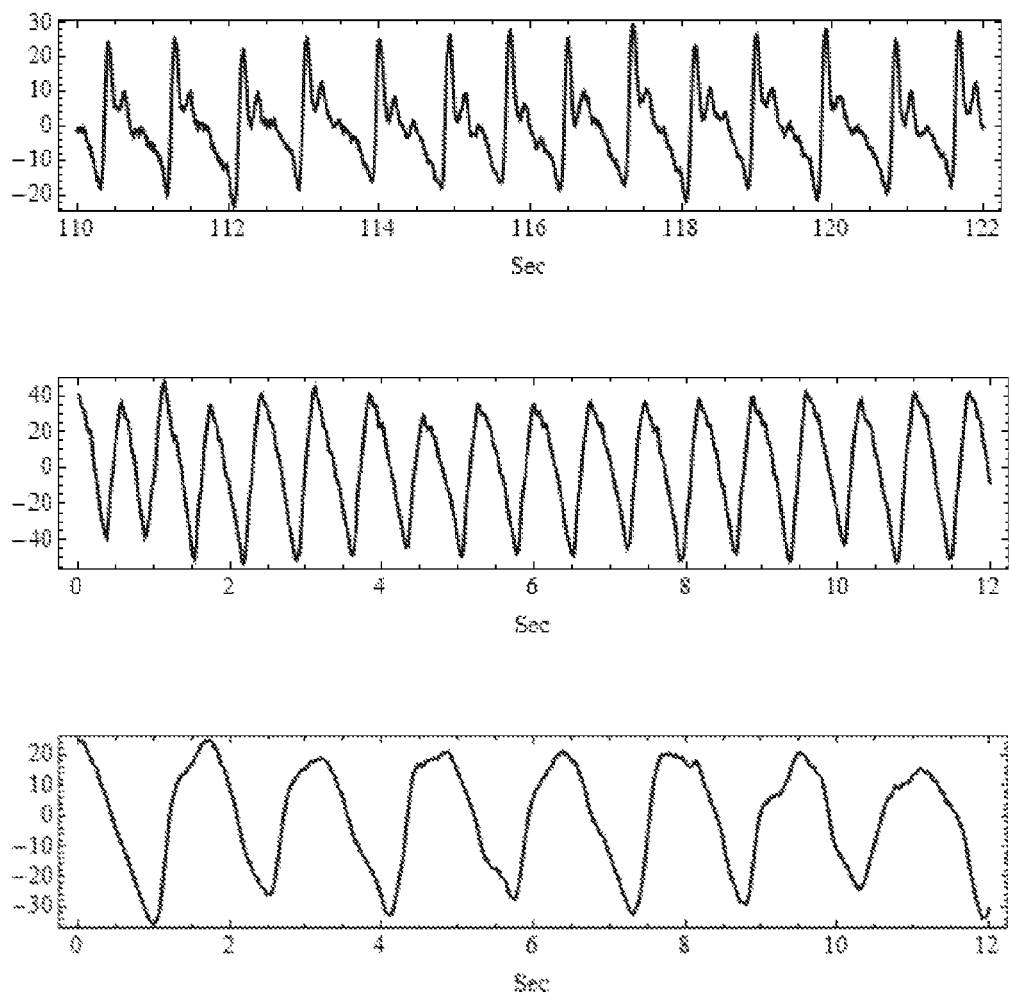
FIG. 9b is an illustration of temporal variations of the absolute value of a measured impedance for three different subjects.

FIG. 9b shows three trace of the temporal variations of the pulse pressures in mmHg relative to the mean arterial pressure, one for each of three different subjects measured with electrodes placed between the Biceps and Triceps muscles. Each electrode area is around 400 $mm^2$ and the spacing between the centres of the electrodes is around 30 mm. The top trace is the result for a healthy young male; the middle trace is for an elderly female with a very high systolic blood pressure and a low body mass index; the bottom trace is for a middle aged male with a very high blood pressure and a very high body mass index.

Figure 10A:
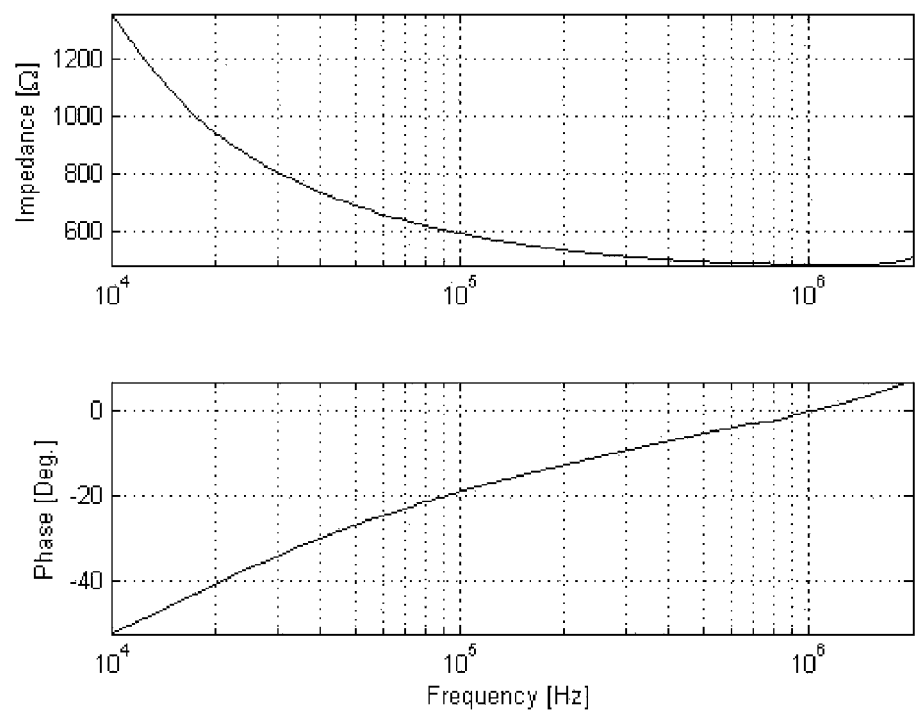
FIG. 10a shows the measured (solid line) and fitted mean impedances for two electrode as a function of the excitation frequency.

FIG. 10a shows the measured mean impedance characterized by an absolute value and a phase for electrodes on the patch placed on the inside of the upper arm as a function of the excitation frequency. The electrode areas are 400 $mm^2$ and the spacing between the centers of the electrodes perpendicular to the artery is 50 mm.

Figure 10B:
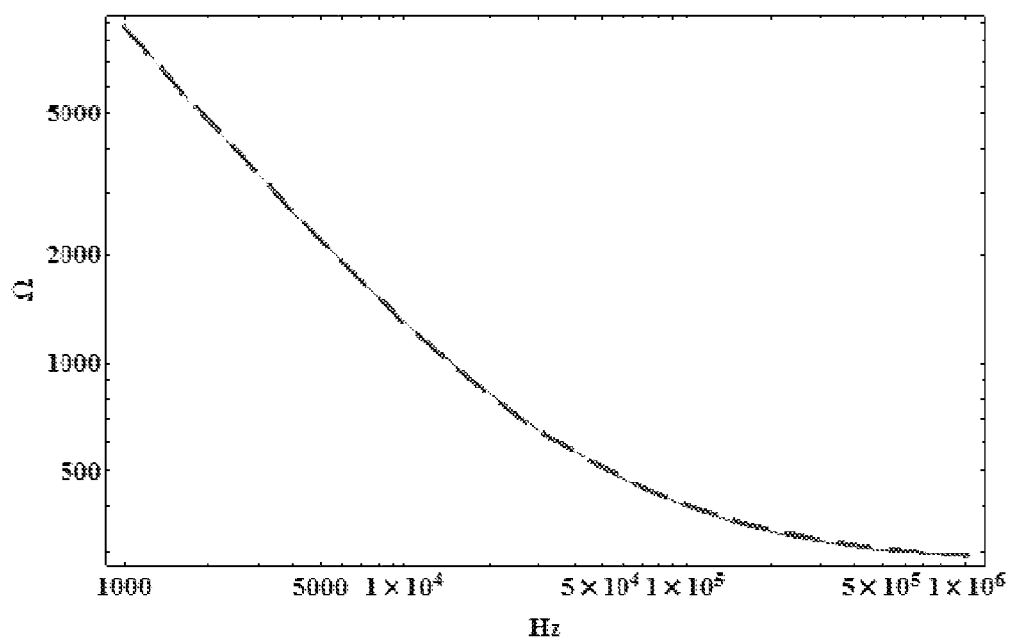
FIG. 10b shows the measured absolute value of the impedance (solid line) with two electrodes and the function fitted to the measured values.

FIG. 10b shows the measured absolute value of the impedance (solid line) in Ohms measured at the upper arm with electrodes as in FIG. 10a. as a function of the frequency in the range between 1 kHz to 1 MHz and also shows the function fitted to the measured impedance (broken line), which thus demonstrates a very good fit to the established model.

Figure 11:
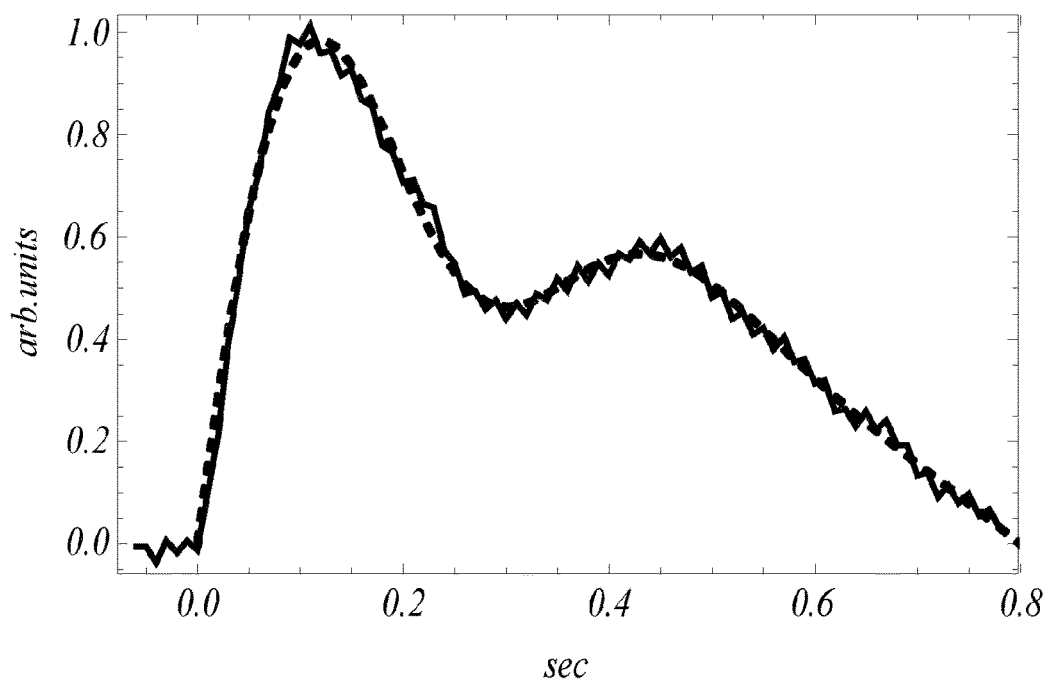
FIG. 11 shows a measured and a fitted single pulse.

FIG. 11 shows a measured and a fitted single pulse. The pulse is measured at the Radial artery.

The invention claimed is:

1. A method of determining at least one cardiovascular quantity of a mammal,
comprising:
determining or estimating a mean diameter of a vessel at a measuring site by:
applying a plurality of electrical oscillating signals selected from an oscillating current and an oscillating voltage to at least one set of electrodes, wherein the plurality of electrical oscillating signals comprises at least two different excitation frequencies and wherein electric field lines between the at least one set of electrodes penetrate the vessel at the measuring site; and
determining an impedance between the at least one set of electrodes for each excitation frequency;
determining an elasticity related quantity of the vessel at the measuring site;
determining a distension of the vessel at the measuring site; and
calculating the at least one cardiovascular quantity from the determined mean diameter, the elasticity related quantity and the distension of the vessel at the measuring site.

2. The method as claimed in claim 1, wherein the vessel is an artery selected from a Brachial artery, a Radial artery, an Ulnar artery, a Femoral artery, a Digital artery and a Carotid artery.

3. The method as claimed in claim 1, wherein the method comprises applying the at least one set of electrodes comprising at least two electrodes within a selected distance to the measuring site.

4. The method as claimed in claim 3, wherein each of the electrodes of the at least one set of electrodes being attached to a skin surface of the mammal.

5. The method as claimed in claim 4, further comprising determining at least one impedance parameter of the at least one set of electrodes as a function of time.

6. The method as claimed in claim 3, wherein the method further comprises determining at least one impedance parameter by measuring over the at least one set of electrodes, where an excitation electrode set and a detection electrode set constitutes the same set.

7. The method as claimed in claim 1, wherein the method comprises applying at least two sets of electrodes, a first and a second electrode set, within a selected distance to the measuring site, applying an electrical signal selected from an oscillating current and an oscillating voltage of at least one excitation frequency to the first set of electrodes, and determining at least one impedance parameter by measuring over the second set of electrodes, where an excitation electrode set and a detection electrode set constitute the first set and second set, respectively.

8. The method as claimed in claim 1, wherein the determination of the mean diameter comprises determining the mean diameter using multi frequency excitation.

9. The method as claimed in claim 1, wherein the determination of the mean diameter of the vessel at the measuring site comprises providing a priory estimation of a structure of a cross-section anatomy at the measuring site and adjacent region penetrated by the field lines of the at least one set of electrodes, setting up a set of mathematical formulas based on this priory estimation by an equivalent circuit for the impedance between the at least one set of electrodes, where the mathematical formulas divide electric field lines into at least one length part of field lines passing through skin, one length part of field lines passing through fat layer, one length part of field lines passing through muscles and one length part of field lines passing through the vessel and determining an actual length part of field lines passing through the vessel based on the determined impedance between the at least one set of electrodes at the least two different excitation frequencies and the set of mathematical formulas.

10. The method according to claim 1 wherein four electrodes are applied and an excitation current is applied to at least a first set of electrodes comprising at least two electrodes that are configured in such a way that when applied to skin they are displaced both in a direction of an artery and perpendicular to the artery, and a voltage is measured on at least a second set of electrodes comprising at least two electrodes that are configured in such a way that when applied to the skin they are displaced also in the direction of the artery and perpendicular to the artery, and configured in such a way that the diagonals of the first and second set of electrodes are crossing.

11. The method as claimed in claim 1, wherein the determination of the elasticity related quantity of the vessel at the measuring site comprises determining a pulse wave velocity in the vessel at the measuring site, wherein the determination of the pulse wave velocity in the vessel at the measuring site comprises placing at least two sensors with a selected mutual distance along a length section L of the vessel comprising at least a part of the measuring site, and determining the pulse as a function of time by each sensor and thereby determining the pulse wave velocity.

12. The method as claimed in claim 11, wherein there is provided the at least two sensors, a first sensor comprising a first set of electrodes and a second sensor comprising a second set of electrodes, the respective sets of electrodes being electrically connected in electrical circuits such that electric field lines between the respective set of electrodes penetrate the vessel at respectively a first pulse wave sensing site and a second pulse wave sensing site.

13. The method as claimed in claim 1, wherein there is provided at least three electrode sets, a first electrode set being detection electrodes, a second electrode set being detection electrodes, and a third electrode set being excitation electrodes, the third electrode set being placed such that at least the electrical field lines excited from the third set of electrodes penetrate the vessel at the measuring site.

14. The method as claimed in claim 13 wherein the third set of electrodes is placed in between the first and second electrode sets.

15. The method as claimed in claim 1, further comprising determining the impedance of two respective sets of electrodes as a function of time and determining a temporal displacement of one impedance signal with respect to the other impedance signal.

16. The method as claimed in claim 1, where the determined cardiovascular quantity is a differential blood pressure, which is the difference between a systolic and a diastolic pressure, which differential blood pressure is determined from the velocity v of a pulse wave in the vessel at the measuring site by applying the following equation $$v \cong \sqrt{\frac{\Delta P}{\Delta A} \frac{A}{\rho}},$$

where ΔP is the differential blood pressure, ΔA is the distension of the vessel, ρ the blood density, and A is expressed by the mean vessel cross-section area.

17. The method as claimed in claim 1, wherein the determination of the distension of the vessel at the measuring site comprises an electrical circuit comprising the at least one set of electrodes such that electric field lines between the at least one set of electrodes penetrate the vessel at the measuring site, and determining a temporal variation of impedance of the at least one set of electrodes.

18. The method as claimed in claim 1 wherein the method comprises applying the at least one set of electrodes within a selected distance to the measuring site, applying an electrical oscillating signal to the at least one set of electrodes and determining at least one impedance parameter selected from mean impedance, minimum impedance, maximum impedance, temporal variations of impedance, impedance as a function of time or any combination thereof over the at least one set of electrodes.

19. The method as claimed in claim 18, wherein the method comprises determining or estimating temporal spacing between pulses of the mammal, determining the mean impedance using a bridge and automatic balancing the bridge through a feedback loop with a loop response time that is at least as large as the temporal spacing between pulses by adjusting at least two resistance components of the bridge.

20. The method as claimed in claim 18, wherein the method comprises determining or estimating temporal spacing between pulses of the mammal, determining the temporal variation of impedance using a bridge and automatic balancing the bridge through a feedback loop with a loop response time that is at least as large as the temporal spacing between pulses, the method comprises determining temporal variations of the imbalance of the bridge.

21. The method as claimed in claim 1, wherein
the determination of mean diameter,
the determination of the elasticity related quantity,
the determination of distension of the vessel, and
the determinations of two thereof, or the determination of all three thereof is/are based on determination of at least one impedance parameter selected from mean impedance, minimum impedance, maximum impedance, temporal variations of impedance, impedance as a function of time or any combination thereof over the at least one set of electrodes.

22. The method as claimed in claim 1, wherein the calculation of the at least one cardiovascular quantity from the determined mean diameter, the elasticity related quantity, and the distension of the vessel at the measuring site comprises calculating a differential blood pressure, calculating a systolic blood pressure, calculating a diastolic pressure or calculating a vascular compliance.

23. The method as claimed in claim 1, wherein the method further comprises determining at least one additional dimension of the vessel at the measuring site, selected from the thickness of a vessel wall, a maximum diameter of the vessel, a minimum diameter of the vessel, a temporal variation of the vessel diameter or vessel diameter as a function of time.

24. The method as claimed in claim 1, wherein the method further comprises determining a pulse rate.

25. The method as claimed in claim 1, wherein the method is non-invasive.

26. The method as claimed in claim 1, not comprising application of pressure to the vessel.

27. The method as claimed in claim 1, where any one of pulse amplitude, pulse pressure, or pulse rate selected, is determined by applying a counter pressure for calibration purposes.

28. A method of determining at least one cardiovascular quantity of a mammal, the method comprises:
determining or estimating a mean diameter of a vessel at a measuring site;
applying at least one set of electrodes comprising at least two electrodes within a selected distance to the measuring site;
applying an electrical oscillating signal to the electrodes such that electric field lines from the electrodes penetrate the vessel at the measuring site;
determining at least one impedance parameter of a detection set of electrodes as a function of time;
determining an elasticity related quantity of the vessel at the measuring site;
determining a distension of the vessel at the measuring site; and
calculating the at least one cardiovascular quantity from the determined mean diameter, the elasticity related quantity and the distension of the vessel at the measuring site,
wherein the determination of the at least one impedance parameter is performed using signal processing by at least one of a voltage follower and an instrumentation amplifier for sensing and amplifying the signal from the detection electrodes, and at least one mixer for demodulation of the signal by quadrature detection, and amplifying the demodulated signal, comprising an in-phase signal and the quadrature signal, by a known value.

29. A cardiovascular quantity system for determining at least one cardiovascular quantity in a vessel of a mammal, the cardiovascular quantity system comprising:
a plurality of sets of electrodes where each set of electrodes comprising at least two electrodes that can be attached to a skin surface of the mammal such that capacitive coupling through the skin surface and between the electrodes of the plurality of sets of electrodes is provided when an electrical signal is applied over the electrodes at a measuring site of the vessel;
electrical devices apply the electrical signal comprising an electric oscillating signal over the plurality of sets of electrodes; and
at least one processor and a memory unit arranged to receive electrical response signals from the plurality of sets of electrodes; wherein the at least one processor is coupled to the plurality of sets of electrodes and is configured with software instructions to calculate the at least one cardiovascular quantity by:
determining or estimating a mean diameter of the vessel at the measuring site by:
applying a plurality of electrical oscillating signals selected from an oscillating current and an oscillating voltage to at least one set of electrodes, wherein the plurality of electrical oscillating signals comprises at least two different excitation frequencies and wherein electric field lines between the at least one set of electrodes penetrate the vessel at the measuring site; and determining an impedance between the at least one set of electrodes for each excitation frequency;

determining an elasticity related quantity of the vessel at the measuring site;

determining a distension of the vessel at the measuring site; and calculating the at least one cardiovascular quantity from the determined mean diameter, the elasticity related quantity and the distension of the vessel at the measuring site.

* * * * *